(12) United States Patent
Bonaventura et al.

(10) Patent No.: US 11,739,063 B2
(45) Date of Patent: Aug. 29, 2023

(54) DREADD ACTUATORS

(71) Applicants: The United States of America, as represented by the Secretary, Department of Health and Human Services, Bethesda, MD (US); The Johns Hopkins University, Baltimore, MD (US)

(72) Inventors: Jordi Bonaventura, Baltimore, MD (US); Juan Luis Gomez, Frederick, MD (US); Andrew Horti, Ellicott City, MD (US); Feng Hu, Lutherville, MD (US); Michael Michaelides, Baltimore, MD (US); Martin Pomper, Baltimore, MD (US); Marta Sanchez-Soto, Odenton, MD (US)

(73) Assignees: The United States of America, as represented by the Secretary, Department of Health and Human Services, Bethesda, MD (US); The Johns Hopkins University, Baltimore, MD (US)

(*) Notice: Subject to any disclaimer, the term of this patent is extended or adjusted under 35 U.S.C. 154(b) by 229 days.

(21) Appl. No.: 16/968,437

(22) PCT Filed: Feb. 6, 2019

(86) PCT No.: PCT/US2019/016892
§ 371 (c)(1),
(2) Date: Aug. 7, 2020

(87) PCT Pub. No.: WO2019/157083
PCT Pub. Date: Aug. 15, 2019

(65) Prior Publication Data
US 2020/0399228 A1    Dec. 24, 2020

Related U.S. Application Data

(60) Provisional application No. 62/627,527, filed on Feb. 7, 2018.

(51) Int. Cl.
*C07D 243/38* (2006.01)
*A61K 49/10* (2006.01)

(52) U.S. Cl.
CPC ........... *C07D 243/38* (2013.01); *A61K 49/10* (2013.01)

(58) Field of Classification Search
CPC .............................. C07D 243/38; A61K 49/10
See application file for complete search history.

(56) References Cited

FOREIGN PATENT DOCUMENTS

| | | | |
|---|---|---|---|
| RU | 2010118923 A | 11/2011 | |
| RU | 2441867 C2 | 2/2012 | |
| WO | WO 96/18622 A1 | 6/1996 | |
| WO | WO 2013-070107 A1 | 3/2013 | |
| WO | WO 2017-049252 A1 | 3/2017 | |

OTHER PUBLICATIONS

De Paulis, T., C. R. Betts and H. Smith, "Synthesis of Clozapine Analogues and Their Affinity for Clozapine and Spiroperidol Binding Sites in Rat Brain", Journal of Medical Chemistry (1981), 24(9), pp. 1021-1026 (Year: 1981).*
Chen et al., "The First Structure-Activity Relationship Studies for Designer Receptors Exclusively Activated by Designer Drugs", ACS Chemical Neuroscience, 6: pp. 476-484. (Year: 2015).*
Patani, G. and E. LaVoie, "Bioisosterism: A Rational Approach in Drug Design", Chem. Rev. (1996), 96: pp. 3147-3176. (Year: 2011).*
Bonaventura et al., "Novel high affinity DREADD ligands for in vivo PET imaging", Poster (2011). (Year: 2011).*
Ji et al., "Multimodal Imaging for DREADD-Expressing Neurons in Living Brain and Their Application to Implantation of iPSC-Derived Neural Progenitors", J. Neurosci. (2016), 36 (45), pp. 11544-11558. (Year: 2016).*
Bonaventura et al., "809.07/VV49—New high affinity DREADD ligands for In vivo PET imaging," Session 809—Optical Probes: Functional Readouts (2017) (Abstract).
Bonaventura et al., "Novel high affinity DREADD ligands for in vivo PET imaging," Poster (2011).
Burki et al., "Effects of Clozapine and other Dibenzo-epines on Central Dopaminergic and Cholinergic Systems," *Arzneimittel Forschung—Drug Research*, 27(II), Nr. 8, 1561-1565 (1977).
Cascini et al., "¹²⁴Iodine: A Longer-Life Positron Emitter Isotope—New Opportunities in Molecular Imaging," *BioMed Research International*, 672094 (2014).

(Continued)

*Primary Examiner* — Joseph R Kosack
*Assistant Examiner* — Sagar Patel
(74) *Attorney, Agent, or Firm* — Leydig, Voit & Mayer, Ltd.

(57) ABSTRACT

Disclosed is a compound of formula (I) in which R1, R2, and R3 are as described herein. Also provided are pharmaceutical compositions comprising the compound of formula (I) and methods of using the compound of formula (I), including a method of treating a disease or disorder and a method for effectuating a G-protein coupled receptor (GPCR)-mediated response in a subject.

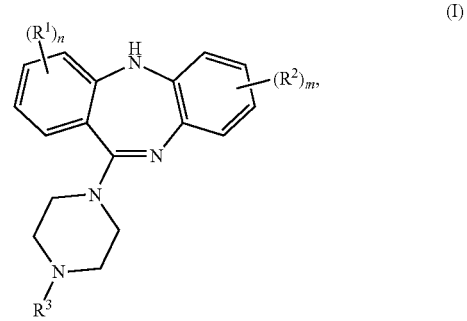

16 Claims, 14 Drawing Sheets

(56) References Cited

OTHER PUBLICATIONS

Chen et al., "The First Structure-Activity Relationship Studies for Designer Receptors Exclusively Activated by Designer Drugs," *ACS Chemical Neuroscience*, 6:46-484 (2015).

European Patent Office, International Search Report in International Patent Application No. PCT/US2019/016892, dated Apr. 1, 2019.

European Patent Office, Written Opinion in International Patent Application No. PCT/US2019/016892, dated Apr. 1, 2019.

Joshua et al., "Synthesis and biodistribution of 8-iodo-11-(4-methyl-piperazino)-5H-dibenzo[b,e][1,4]-diazepine: lozapine," *Bioorganic & Medicinal Chemistry Letters*, 17: 4066-4069 (2007).

Lundberg et al., "Sriatal and frontal cortex binding of 11-C-labelled clozapine visualized by positron emission tomography (PET) in drug-free schizophrenics and healthy volunteers," *Psychopharmacology*, 99: 8-12 (1989).

Michaelides et al., "Whole-brain circuit dissection in free-moving animals reveals cell-specific mesocorticolimbic networks," *The Journal of Clinical Investigation*, 123(12): 5342-5350 (2013).

Mume et al., "Evaluation of ((4-Hydroxyphenyl)ethyl)maleimide for Site-Specific Radiobromination of Anti-HER2 Affibody," *Bioconiugate Chem.*, 16: 1547-1555 (2005).

Nagai et al., "PET imaging-guided chemogenetic silencing reveals a critical role of primate rostromedial caudate in reward evaluation," *Nature Communications*, 7: 13605 (2016).

Roelofs et al., "A novel approach to map induced activation of neuronal networks using chemogenetics and functional neuroimaging in rats: A proof-of-concept study on the mesocorticolimbic system," *NeuroImage*, 156: 109-118 (2017).

Bonaventura et al., "Novel high affinity DREADD ligands for In vivo PET imaging" (Poster), presented at the Neuroscience 2017 meeting, Nov. 15, 2017.

Bonaventura et al., "High-potency ligands for DREADD imaging and activation in rodents and monkeys", *Nature Communications*, vol. 10, No. 4627, pp. 1-12, Oct. 11, 2019.

Bonaventura et al., Supplementary Figures for "High-potency ligands for DREADD imaging and activation in rodents and monkeys", *Nature Communications*, vol. 10, No. 4627, pp. 1-12, Oct. 11, 2019.

\* cited by examiner

DREADD ACTUATORS

CROSS-REFERENCE TO RELATED APPLICATIONS

This patent application is a U.S. National Phase Patent Application of co-pending International Patent Application No. PCT/US2019/016892, filed Feb. 6, 2019, which claims the benefit of U.S. Provisional Patent Application No. 62/627,527, filed Feb. 7, 2018, both of which are hereby incorporated by reference in their entireties.

STATEMENT REGARDING FEDERALLY SPONSORED RESEARCH OR DEVELOPMENT

This invention was made with Government support under project number 1ZIADA000069-02 by the National Institutes of Health, National Institute of Drug Abuse. The Government has certain rights in the invention.

BACKGROUND OF THE INVENTION

The chemogenetic technology Designer Receptors Exclusively Activated by Designer Drugs ("DREADD") is a powerful and versatile approach for remote and transient manipulation of cellular activity in laboratory animals with unique translational potential for clinical therapeutics. DREADD technology uses "designer receptors," namely mutated human muscarinic receptors (namely hM3Dq and hM4Di), which are not activated by acetylcholine or other endogenous neurotransmitters, but are activated by the "designer drug" clozapine n-oxide ("CNO"), an otherwise inert and inactive metabolite of clozapine.

Despite advancements in the field of DREADD technology, there exists a need for improved DREADD compositions and methods. There is also a need for new compounds which can be administered to treat diseases or disorders in subjects. Further, there is a need for methods of treating subjects suffering from disease or disorders.

BRIEF SUMMARY OF THE INVENTION

An embodiment of the invention provides a compound of formula (I)

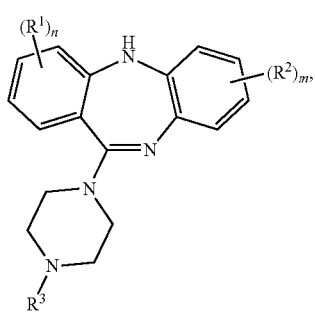

(I)

in which $R^1$, $R^2$, and $R^3$ are as described herein.

An embodiment of the invention further provides a pharmaceutical composition comprising a compound of any one of the embodiments of the invention and a pharmaceutically acceptable carrier.

Another embodiment of the invention provides methods of treating a disease or disorder in a subject by administering to the subject a compound of any one of the embodiments of the invention, a pharmaceutically acceptable salt thereof, or a composition comprising a compound of any one of the embodiments of the invention.

A further embodiment of the invention provides methods of effectuating a G-protein coupled receptor ("GPCR")-mediated response in a subject by administering to a subject a compound of any one of the embodiments of the invention, a pharmaceutically acceptable salt thereof, or a composition comprising a compound of any one of the embodiments of the invention.

It was surprisingly discovered that compounds of formula (I) have a high affinity for hM3Dq and hM4Di receptors (as compared to the affinity of one or both of (i) CNO and (ii) analogs of clozapine disclosed, e.g., compounds 13 and 21 in Chen et al., *ACS Chem. Neuroscience*, (6): 476-484 (2015) for hM3Dq and hM4Di receptors).

It was also surprisingly discovered that compounds of formula (I) exhibit superior brain penetrance in non-human primates (as compared to the brain penetrance of compound 21 of Chen et al., *ACS Chem. Neuroscience*, (6): 476-484 (2015)).

In addition, it was discovered that compounds of formula (I) can be used in DREADD-assisted metabolic mapping (DREAMM) (see Michaelides et al., *J Clin Invest.*, 123(12): 5342-5350 (2013)), while other compounds, such as compound 21 of Chen et al., *ACS Chem. Neuroscience*, (6): 476-484 (2015) are not suitable for DREAMM due to their significant impact on brain metabolic activity (even when no behavior effects are detected).

Further, it was unexpected that the compounds of formula (I) can be labeled with radioactive isotopes with sufficient half-lives that allow for successful in vivo and ex-vivo imaging, as compared to, for example, the short half-life of carbon-11 (only 20 minutes). The increased half-life allows for theranostic methods that involve (1) treating a subject for a disease or disorder with a compound of formula (I) and (2) being able to confirm that the compounds of formula (I) are targeting the appropriate area of the tissue (e.g., brain) and that the hM3Dq and/or hM4Di receptors are located in the appropriate area of the tissue. The theranostic methods will allow those treating the subjects to adjust the levels of compounds administered to the subject for an improved treatment regimen. Further, the labeling of the compound of formula (I) with radioactive isotopes (and then using PET) allows for the technology to be used to treat human subjects because the receptor expression can be monitored on live patients.

Additionally, it was found that by using the compounds of the formula (I), there was no longer a need for the DREADDs to be expressed fused to fluorescent reporter proteins (previously the only way to visualize their location was post-mortem). Therefore, the compounds of the formula (I) eliminate issues such as receptor internalization, toxicity, and undesired immune responses associated with fluorescent reporter proteins. In addition, the compounds of the formula (I) increase reliability and reproducibility across species as compared to the use of reporter proteins while allowing quantification of receptor expression and validation of accurate DREADD placement.

Another unexpected benefit is that the compounds of formula (I) containing $^{19}F$ can be used as contrast agents in magnetic resonance imaging ("MRI") and magnetic resonance spectroscopy ("MRS"), because $^{19}F$ is not endogenous in living organisms. MRS uses the MRI data and measures biochemical changes in the brain by comparing the chemical composition of the imaged subject's tissue to the chemical composition of normal tissue of the same tissue type. This discovery provides yet another non-invasive imaging procedure, which provides a powerful tool for treating subjects.

DETAILED DESCRIPTION OF THE INVENTION

Figure 1:
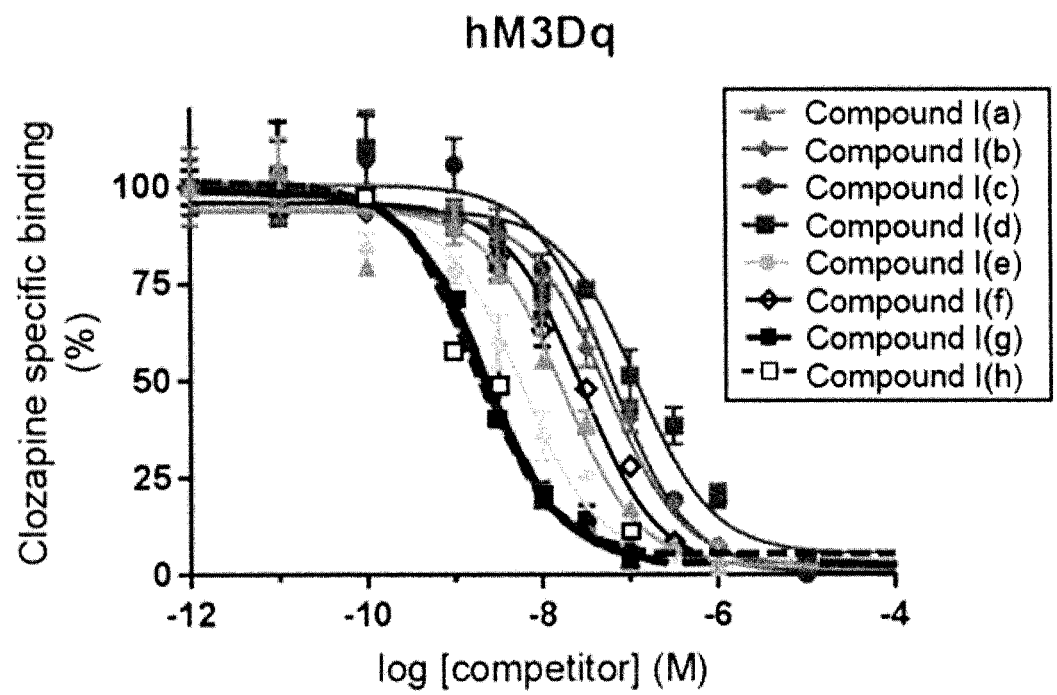
FIG. 1 is a graph showing the binding affinity of Compounds I(a)-I(h) to hM3Dq receptor as compared to clozapine's specific binding to hM3Dq receptor.

The invention provides a compound of formula (I):

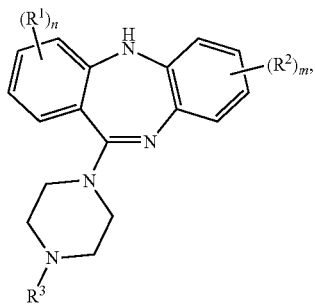

(I)

wherein $R^1$ and $R^2$ are the same or different and each is a halo, $R^3$ is methyl or ethyl, n and m are the same or different and each is an integer from 0 to 2, wherein n+m is 1 to 4, or a pharmaceutically acceptable salt thereof.

In any of the embodiments herein, the term "halo" refers to a halogen selected from fluorine, chlorine, bromine, and iodine. Preferably, the halos of formula (I) are selected from fluoro, chloro, and a combination thereof.

In some embodiments of the present invention, the compound of formula (I) is a compound of formula (II):

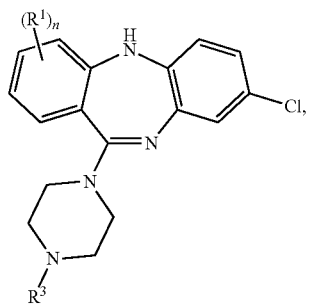

(II)

wherein $R^1$ is fluoro, bromo, or iodo, $R^3$ is methyl or ethyl, and n is 1 or 2, or a pharmaceutically acceptable salt thereof. Preferably, $R^1$ is fluoro. More preferably, $R^1$ is fluoro, and n is 1.

In other embodiments of the present invention, the compound of formula (I) is a compound of formula (III):

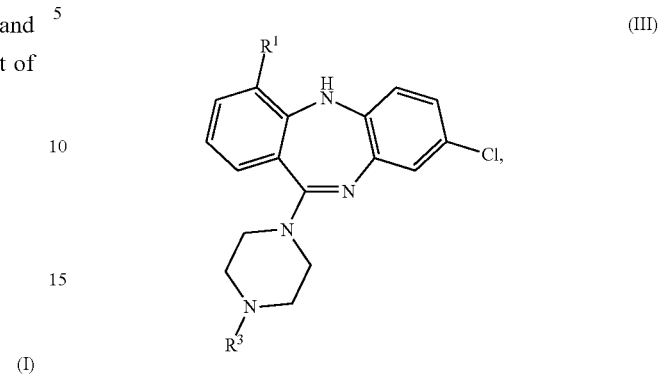

(III)

wherein $R^1$ is fluoro, bromo, or iodo, $R^3$ is methyl or ethyl, or a pharmaceutically acceptable salt thereof. Preferably, $R^1$ is fluoro. More preferably, $R^1$ is fluoro and $R^3$ is ethyl.

Specific examples of the compound of formula (I) are:

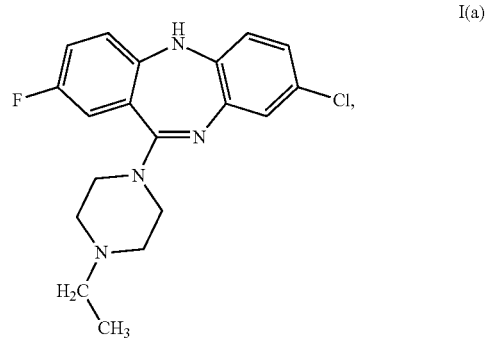

I(a)

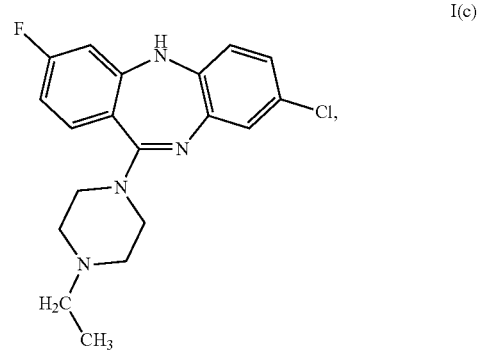

I(c)

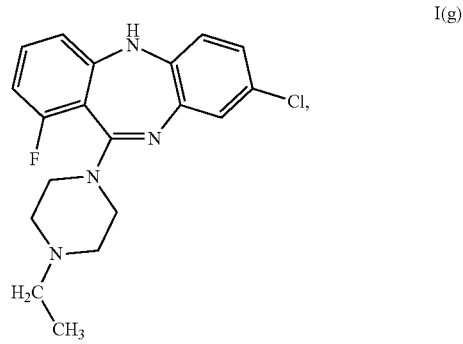 [SMILES: CCN1CCN(C2=Nc3cc(Cl)ccc3Nc3cccc(F)c32)CC1]

I(g)

-continued

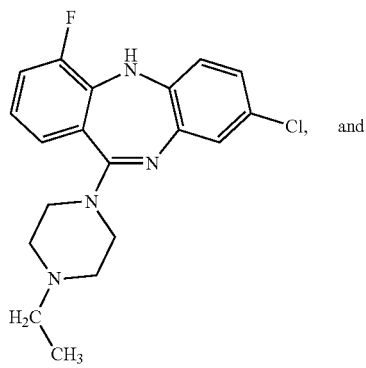

and

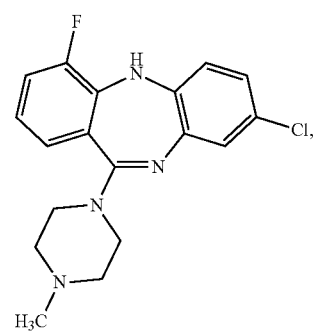

or a pharmaceutically acceptable salt thereof.

Preferably, the compound of formula (I) is:

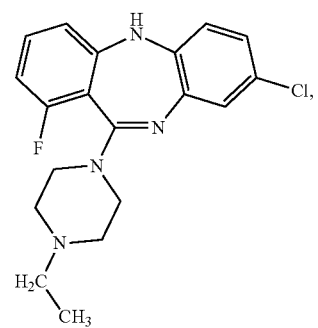

or a pharmaceutically acceptable salt thereof.

Preferably, the compound of formula (I) is:

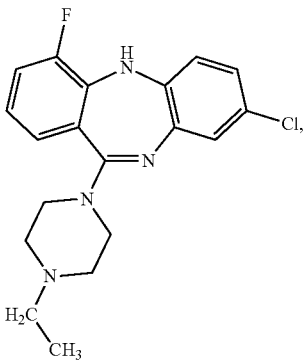

or a pharmaceutically acceptable salt thereof.

Another specific example of the compound of formula (I) is:

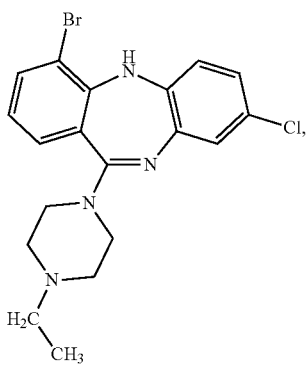

or a pharmaceutically acceptable salt thereof.

Another specific example of the compound of formula (is:

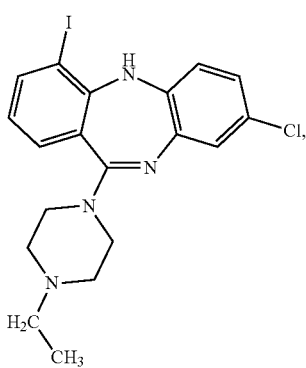

or a pharmaceutically acceptable salt thereof.

In another embodiment of the present invention, the compound of formula (I) is a compound of formula (V):

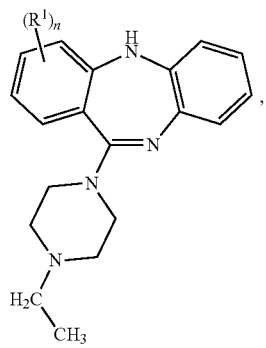
(V)

wherein R¹ is fluoro, and n is 1, or a pharmaceutically acceptable salt thereof.

Specific examples of the compound of formula (are:

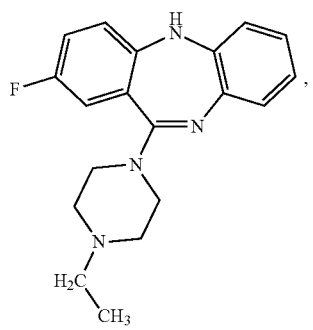
I(b)

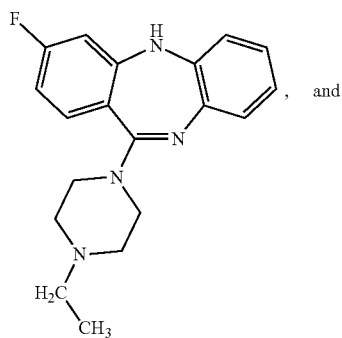
I(d)
, and

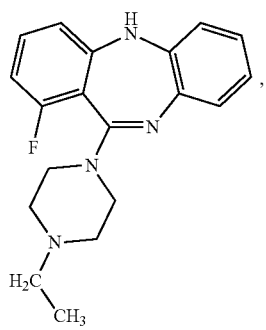
I(e)

or a pharmaceutically acceptable salt thereof.

Another specific example of the compound of formula (I) is:

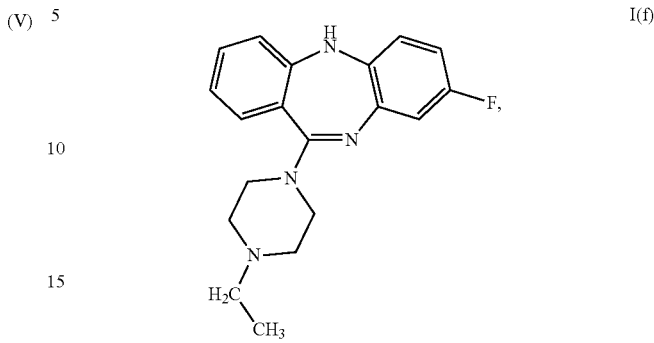
I(f)

or a pharmaceutically acceptable salt thereof.

The subscripts "m" and "n" represent the number of substituents (e.g., "F," "Br," "I," or "Cl"), in which each instance of the halogen can be the same or different. The subscripts m and n can be the same or different and each is either 0 or an integer from 1-4 (i.e., 1, 2, 3, or 4). When m is 0, then the corresponding substituent is not present in the compound of formula (I). When m is 0, then n is 1-4 in the compound of formula (I). When n is 0, then the corresponding substituent is not present in the compound of formula (I). When n is 0, then m is 1-4 in the compound of formula (I).

The compound of formula (I) can have any suitable stereochemistry and can be in the form of a single stereoisomer, a mixture of two or more stereoisomers (e.g., an epimer, a mixture of diastereomers and/or enantiomers, a racemic mixture).

In any of the embodiments above, the phrase "salt" or "pharmaceutically acceptable salt" is intended to include nontoxic salts synthesized from the parent compound and which contain a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used. Generally, nonaqueous media such as ether, ethyl acetate, ethanol, isopropanol, or acetonitrile are typical. Lists of suitable salts are found in *Remington's Pharmaceutical Sciences*, 22$^{nd}$ revised ed., Pharmaceutical Press, 2012, and *Journal of Pharmaceutical Science*, 104: 12 (2015). For example, a salt of an alkali metal (e.g., sodium or potassium), alkaline earth metal (e.g., calcium), or ammonium can be provided.

In a further embodiment, the invention provides compounds comprising a radioactive isotope. Preferably, the radioactive isotope is suitable for PET imaging. Preferably, the radioactive isotope is selected from the group consisting of fluorine-18 ($^{18}$F), iodine-124 ($^{124}$I), and bromine-76 ($^{76}$B). Preferably, the radioactive isotope is fluorine-18 ($^{18}$F). Preferably, at least one halo of a compound of formula (I) is a radioactive isotope.

In a further embodiment, the invention provides compounds comprising a radioactive isotope that has a half-life that allows for the compound of formula (I) to be administered to a live subject and for the live subject to be imaged by PET. In an embodiment, the radioactive isotope has a half-life of more than about 20 minutes. In a related embodiment, the radioactive isotope has a half-life of more than 25 minutes (e.g., more than about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160 minutes, about 3 hours, about 5 hours, about 15 hours, about 24 hours, about 36 hours, about 48 hours, about 60 hours, about 72 hours, or about 80 hours). Having a half-life of at least about 25 minutes allows for the compound of formula (I) to be prepared, be administered to the patient, and allows for the patient to be positioned for PET imaging.

The compounds of formula (I) can be prepared by any suitable synthetic methodology, including using techniques known in the art. Suitable methods are set forth in the general procedures described below (e.g., Example 1).

Any suitable $^{18}$F-containing label may be used. Preferably, the radiolabel is $^{18}$F. $^{18}$F has a half-life ($t_{1/2}$) of 110 minutes, emits β+ particles at an energy of 635 keV, and is 97% abundant. $^{18}$F may be obtained from cyclotrons after bombardment of $^{18}$O-enriched water with protons. The enriched water containing H-$^{18}$F may be neutralized with a base having a counter-ion that is any alkali metal (M), such as potassium or another monovalent ion, and the water may be evaporated off to give a residue of M-$^{18}$F, which may be taken up in an organic solvent for further use. In general, the counter-ion may be selected to enable the fluoride ion to react rapidly in an organic phase with a halogen. Potassium may be used as a counter-ion because it is cheaper than cesium. However, with carrier-free $^{18}$F, trivial amounts of counter-ion are required, and the counter-ion cost may be minimal.

Cesium may be useful as a counter ion because it is a larger ion with a more diffuse charge. Accordingly, cesium has looser ionic interactions with the small fluoride atom, and therefore does not interfere with the nucleophilic properties of the fluoride ion. For similar reasons, potassium may be preferred to sodium, and, in general, the suitability of a Group Ia metal as a counter-ion in accordance with the present invention increases down the periodic table. Group Ib reagents, such as silver, also may be useful as counter-ions. Further, organic phase transfer-type ions, such as tetraalkylammonium salts, also may be used as counter-ions.

Fluoride can have a tendency to become hydrated and lose its nucleophilic character. To minimize this, the labeling reaction may be preferably performed under anhydrous conditions. For example, fluoride (as potassium fluoride or as a complex with any of the other counter-ions discussed above) may be placed in organic solvents, such as acetonitrile or tetrahydrofuran. With the help of agents which bind to the counter-ion, such as KRYPTOFIX™ 2.2.2 (4,7,13,16,21,24-hexaoxa-1,10-diazabicyclo[8.8.8]-hexacosane), the fluoride ion may be very nucleophilic in these solvents.

Any suitable $^{124}$I-containing label may be used. Preferably, the radiolabel is $^{124}$I. $^{124}$I has a half-life ($t_{1/2}$) of 4.2 days, emits β+ particles and gamma particles, and is 9.1% abundant. $^{124}$I may be purchased commercially, produced in a cyclotron at a PET center, typically starting from $^{124}$Te, or prepared by a synthesis known in the art (e.g., Cascini et al., *BioMed Research International*, 2014: 7 pages (2014)).

Any suitable $^{76}$Br-containing label may be used. Preferably, the radiolabel is $^{76}$Br. $^{76}$Br has a half-life ($t_{1/2}$) of 16 h, emits β+ particles at an energy of 3.98 MeV, emits gamma particles, and is 9.1% abundant. $^{76}$Br may be purchased commercially, produced in a cyclotron at a PET center, or prepared by a synthesis known in the art (e.g., Mume et al., *Bioconjugate Chem.*, 16: 1547-1555 (2005)).

The methods described herein comprise administering a compound of formula (I) or a pharmaceutically acceptable salt thereof in the form of a pharmaceutical composition. An embodiment of the invention provides a pharmaceutical composition comprising at least one compound of formula (I) or a pharmaceutically acceptable salt thereof and a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the embodiments, the compound of formula (I) or a pharmaceutically acceptable salt thereof can be administered orally to a subject in need thereof. Formulations suitable for oral administration can include (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the compound of formula (I) in solution. Suitable preservatives and buffers can be used in such formulations. In order to minimize or eliminate irritation at the site of injection, such compositions may contain one or more nonionic surfactants having a hydrophilic-lipophilic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compound of formula (I) can be made into an injectable formulation. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 19th ed. (2016).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compound of formula (I) or a pharmaceutically acceptable salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention.

The dose administered to the mammal, particularly human and other mammals, in accordance with embodiments of the present invention should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations.

The inventive methods comprise administering an effective amount of a compound of formula (I) or a pharmaceutically acceptable salt thereof. An "effective amount" means an amount sufficient to show a meaningful benefit in an individual, e.g., actuating at least one DREADD, or treatment, healing, prevention, delay of onset, inhibiting, halting, or amelioration of other relevant medical condition(s) and/or symptom associated with a particular disease (e.g., a disease or disorder of the brain). The meaningful benefit observed in the mammal can be to any suitable degree (about 10%, about 20%, about 30%, about 40%, about 50%, about 60%, about 70%, about 80%, about 90%, about 95%, about 99% or more). In some aspects, one or more symptoms of the disease (e.g., a disease or disorder of the brain) is prevented, reduced, ameliorated, inhibited, halted, or eliminated subsequent to administration of a compound of formula (I) or a pharmaceutically acceptable salt thereof, thereby effectively treating the disease (e.g., a disease or disorder of the brain) to at least some degree.

Effective amounts may vary depending upon the biological effect desired in the individual, condition to be treated, and/or the specific characteristics of the compound of formula (I) or a pharmaceutically acceptable salt thereof, and the individual (e.g., a 70 kg patient on average). In this respect, any suitable dose of the compound of formula (I) or a pharmaceutically acceptable salt thereof can be administered to the subject (e.g., human), according to the type of disease (e.g., a disease or disorder of the brain) to be treated. Various general considerations taken into account in determining the "effective amount" are known to those of skill in the art and are described, e.g., in Gilman et al., eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I) or a pharmaceutically acceptable salt thereof desirably comprises about 0.001 mg per kilogram (kg) of the body weight of the mammal (mg/kg) to about 400 mg/kg. The minimum dose is any suitable amount, such as about 0.001 mg/kg, about 0.005 mg/kg, about 0.0075 mg/kg, about 0.01 mg/kg, about 0.05 mg/kg, about 0.075 mg/kg, about 0.1 mg/kg, about 0.15 mg/kg, about 0.2 mg/kg, about 0.4 mg/kg, about 0.75 mg/kg, about 1 mg/kg, about 2 mg/kg, about 3 mg/kg, about 5 mg/kg, about 10 mg/kg, about 15 mg/kg, about 20 mg/kg, about 30 mg/kg, about 50 mg/kg, about 60 mg/kg, about 75 mg/kg, about 100 mg/kg, about 150 mg/kg, about 175 mg/kg, about 200 mg/kg, about 250 mg/kg, about 275 mg/kg, or about 300 mg/kg). The maximum dose is any suitable amount, such as about 350 mg/mg, about 300 mg/kg, about 275 mg/kg, about 250 mg/kg, about 200 mg/kg, about 175 mg/kg, about 150 mg/kg, about 100 mg/kg, about 75 mg/kg, about 60 mg/kg, about 50 mg/kg, about 30 mg/kg, about 20 mg/kg, about 15 mg/kg, about 10 mg/kg, about 5 mg/kg, about 3 mg/kg, about 2 mg/kg, about 1 mg/kg, about 0.75 mg/kg, about 0.4 mg/kg, or about 0.2 mg/kg). Any two of the foregoing minimum and maximum doses can be used to define a close-ended range or can be used singly to define an open-ended range.

The pharmaceutical composition also may comprise an anti-psychotic agent other than the compound of formula (I). Suitable anti-psychotic agents are selected from the group consisting of Acetophenazine Maleate, Alentemol Hydrobromide, Alpertine, Azaperone, Batelapine Maleate, Benperidol, Benzindopyrine Hydrochloride, Brofoxine, Bromperidol, Bromperidol Decanoate, Butaclamol Hydrochloride, Butaperazine, Butaperazine Maleate, Carphenazine Maleate, Carvotroline Hydrochloride, Chlorpromazine, Chlorpromazine Hydrochloride, Chlorprothixene, Cinperene, Cintriamide, Clomacran Phosphate, Clopenthixol, Clopimozide, Clopipazan Mesylate, Cloroperone Hydrochloride, Clothiapine, Clothixamide Maleate, Cyclophenazine Hydrochloride, Droperidol, Etazolate Hydrochloride, Fenimide, Flucindole, Flumezapine, Fluphenazine Decanoate, Fluphenazine Enanthate, Fluphenazine Hydrochloride, Fluspiperone, Fluspirilene, Flutroline, Gevotroline Hydrochloride, Halopemide, Haloperidol, Haloperidol Decanoate, Iloperidone, Imidoline Hydrochloride, Lenperone, Mazapertine Succinate, Mesoridazine, Mesoridazine Besylate, Metiapine, Milenperone, Milipertine, Molindone Hydrochloride, Naranol Hydrochloride, Neflumozide Hydrochloride, Ocaperidone, Olanzapine, Oxiperomide, Penfluridol, Pentiapine Maleate, Perphenazine, Pimozide, Pinoxepin Hydrochloride, Pipamperone, Piperacetazine, Pipotiazine Palmitate, Piquindone Hydrochloride, Prochlorperazine Edisylate, Prochlorperazine Maleate, Promazine Hydrochloride, Quetiapine, Remoxipride, Remoxipride Hydrochloride, Risperidone, Rimcazole Hydrochloride, Seperidol Hydrochloride, Sertindole, Setoperone, Spiperone, Thioridazine, Thioridazine Hydrochloride, Thiothixene, Thiothixene Hydrochloride, Tioperidone Hydrochloride, Tiospirone Hydrochloride, Trifluoperazine Hydrochloride, Trifluperidol, Triflupromazine, Triflupromazine Hydrochloride, and Ziprasidone Hydrochloride.

An embodiment of the invention also provides a method of treating a disease or disorder in a subject in need thereof comprising administering to the subject a compound of formula (I), a pharmaceutically acceptable salt thereof, or a composition comprising the compound of formula (I). The disease or disorder can be any disease or disorder, including a disease or disorder of the brain. Suitable disease or disorders of the brain are selected from the group consisting of Absence of the Septum Pellucidum, Acid Lipase Disease, Acid Maltase Deficiency, Acquired Epileptiform Aphasia, Acute Disseminated Encephalomyelitis, ADHD, Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS—Neurological Complications, Alexander Disease, Alper' Disease, Alternating Hemiplegia, Alzheimer's Disease, Amyotrophic Lateral Sclerosis (ALS), Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder, Autism Spectrum Disorder, Autonomic Dysfunction, Back Pain, Barth Syndrome, Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Bipolar Disorder, Blepharospasm, Bloch-Sulzberger Syndrome, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, CADASIL, Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysms, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome (COFS), Charcot-Marie-Tooth Disease, Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, Colpocephaly, Coma, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Cree encephalitis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia—Multi-Infarct, Dementia—Semantic, Dementia—Subcortical, Dementia, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalopathy (familial infantile), Encephalopathy, Encephalotrigeminal Angiomatosis, Epilepsy (including Benign Rolandic Epilepsy, Childhood Absence Epilepsy, Juvenile Myoclonic Epilepsy, Focal Epilepsy, and Epilepsy characterized by the cause of the seizures such as Epilepsy of Unknown Cause [including pure epilepsies due to single gene disorders and pure epilepsies with complex inheritance]; Symptomatic Epilepsy [including mostly genetic or developmental causation (e.g., childhood epilepsy syndromes, progressive myoclonic epilepsies, neurocutaneous syndromes, other neurologic single gene disorders, disorders of chromosome function, and developmental anomalies of cerebral structure) and mostly acquired causes (e.g., hippocampal sclerosis, perinatal and infantile causes, cerebral trauma, tumor or infection, cerebrovascular disorders, cerebral immunologic disorders, and degenerative and other neurologic conditions)]; Provoked [including provoking factors and reflex epilepsies]; and Cryptogenic (presumed symptomatic nature in which the cause has not been identified)), Epileptic Hemiplegia, Erb's Palsy, Erb-Duchenne and Dejerine-Klumpke Palsies, Essential Tremor, Extrapontine Myelinolysis, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gaucher Disease, Generalized Gangliosidoses, Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barri Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus—Normal Pressure, Hydrocephalus, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaacs' Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kluver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lipoid Proteinosis, Lissencephaly, Locked-In Syndrome, Lou Gehrig's Disease, Lupus—Neurological Sequelae, Lyme Disease—Neurological Complications, Machado-Joseph Disease, Macrencephaly, Megalencephaly, Melkersson-Rosenthal Syndrome, Encephalitis, Meningitis, Menkes Disease, Meralgia Paresthetica, Metachromatic Leukodystrophy, Microcephaly, Migraine, Miller Fisher Syndrome, Mini Stroke, Mitochondrial Myopathy, Moebius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myoclonic Encephalopathy of Infants, Myoclonus, Myopathy—Congenital, Myopathy—Thyrotoxic, Myopathy, Myotonia Congenita, Myotonia, Narcolepsy, Neuroacanthocytosis, Neurodegeneration with Brain Iron Accumulation, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathy—Hereditary, Neurosarcoidosis, Neurosyphilis, Neurotoxicity, Niemann-Pick Disease, Normal Pressure Hydrocephalus, O'Sullivan-McLeod Syndrome, Occipital Neuralgia, Ohtahara Syndrome, Olivopontocerebellar Atrophy, Opsoclonus Myoclonus, Orthostatic Hypotension, Overuse Syndrome, Pain—Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, *Piriformis* Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Prosopagnosia, Pseudo-Torch syndrome, Pseudotoxoplasmosis syndrome, Pseudotumor Cerebri, Psychogenic Movement, Ramsay Hunt Syndrome I, Ramsay Hunt Syndrome II, Rasmussen's Encephalitis, Reflex Sympathetic Dystrophy Syndrome, Refsum Disease—Infantile, Refsum Disease, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Schizophrenia, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjögren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson Disease, Wolman's Disease, X-Linked Spinal and Bulbar Muscular Atrophy, and Zellweger Syndrome. Preferably, the disease or disorder is a disease or disorder related to psychosis (e.g., delusions, hallucinations, paranoia, and/or disordered thought) or a type of epilepsy. Preferably, the disease or disorder is schizophrenia, bipolar disorder, or a type of epilepsy.

As used herein, the term "treat" does not necessarily imply complete elimination of a disease (e.g., a disease or disorder of the brain). Rather, there are varying degrees of treatment of which one of ordinary skill in the art recognizes as having a benefit or therapeutic effect. In this respect, the disease or disorder can be treated to any extent through the present inventive method. For example, in a method of treating a disease or disorder, at least about 10% (e.g., at least about 20%, at least about 30%, or at least about 40%) of the symptoms of the disease or disorder is reduced upon administration of a compound described herein. Preferably, at least about 50% (e.g., at least about 60%, at least about 70%, or at least about 80%) of the symptoms of the disease or disorder is reduced upon administration of a compound described herein. More preferably, at least about 90% (e.g., at least about 95%, at least about 99%, or at least about 100%) of the symptoms of the disease or disorder is reduced upon administration of a compound described herein.

For purposes of the present invention, the subject to be treated typically is a mammal. Mammals include, but are not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swines (pigs) or of the order Perssodactyla, including Equines (horses). In some aspects, the mammals are of the order Primates, Ceboids, or Simioids (monkeys) or of the order Anthropoids (humans and apes). In embodiments of the invention, the mammal is a human.

The invention also provides a method for effectuating a G-protein coupled receptor (GPCR)-mediated response in a subject, the method comprising administering to the subject a vector encoding a DREADD-modified human muscarinic GPCR (hM-DREADD), wherein the modified receptor is selected from the group consisting of hM3Dq and hM4Di, to express the modified receptor, and administering the compound of any one of the embodiments of the present invention, or a pharmaceutically acceptable salt thereof, to the subject. In one embodiment, the modified receptor is hM3Dq. In another embodiment, the modified receptor is hM4Di. In a further embodiment, modified receptors hM3Dq and hM4Di are both administered to the subject.

An embodiment of the invention also provides a method which further includes administering a radioisotope-containing compound of any one of the embodiments of the present invention, or a pharmaceutically acceptable salt thereof, to the subject, and imaging the subject with PET. Any suitable method can be used to capture the gamma rays emitted by the positron-emitting radioisotope.

An embodiment of the invention further provides a method which further includes comparing the level of expression of the modified receptor as determined by PET to a control, and adjusting the amount of therapeutic compound, or a pharmaceutically acceptable salt thereof, that is administered to the subject. The person treating the subject can evaluate the level of expression of the modified receptor by comparing it to a control. A control can be a level of expression that is pre-determined to indicate the successful actuation of the receptor. The person treating the individual can increase or decrease the amount of the therapeutic compound, or a pharmaceutically acceptable salt thereof, that is administered to the subject.

An embodiment of the invention also provides a method that further includes imaging the subject with MRI. An embodiment of the invention also provides a method that further includes imaging the subject with MRI and using MRS data analysis.

An embodiment of the invention further provides a method, which further includes comparing the level of expression of the modified receptor as determined by MRI and/or MRS to a control, and adjusting the amount of therapeutic compound, or a pharmaceutically acceptable salt thereof, that is administered to the subject. The person treating the subject can evaluate the level of expression of the modified receptor by comparing it to a control appropriate for MRI and/or MRS. A control can be a level of expression that is pre-determined to indicate the successful actuation of the receptor. The person treating the individual can increase or decrease the amount of the therapeutic compound, or a pharmaceutically acceptable salt thereof, that is administered to the subject.

The vector encoding a DREADD-modified human muscarinic GPCR (hM-DREADD) may be administered to the subject by any suitable means. Preferably, the vector is administered by injection.

Other modified receptors besides hM3Dq and hM4Di may be used in the embodiments of the present invention. For example, another modified G-protein coupled receptor may be used in may be used in the embodiments of the present invention.

Embodiments of the present subject matter described herein may be beneficial alone or in combination, with one or more other embodiments. Without limiting the foregoing description, certain non-limiting embodiments of the disclosure numbered 1-22 are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiments explicitly provided below:

(1) A compound of formula (I)

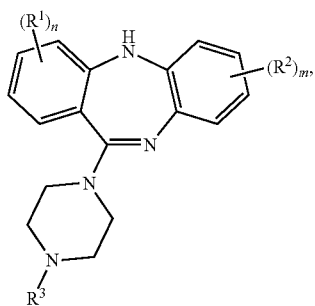

(I)

wherein $R^1$ and $R^2$ are the same or different and each is a halo, $R^3$ is methyl or ethyl, n and m are the same or different and each is an integer from 0 to 2, wherein n+m is 1 to 4, or a pharmaceutically acceptable salt thereof.

(2) The compound of embodiment (1), wherein the halo is selected from fluoro, chloro, and a combination thereof.

(3) The compound of embodiment (1), wherein the compound is of formula (II)

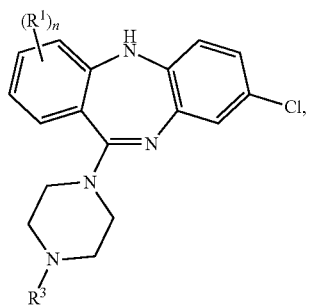

(II)

wherein $R^1$ is fluoro, bromo, or iodo, $R^3$ is methyl or ethyl, and n is 1 or 2, or a pharmaceutically acceptable salt thereof.

(4) The compound of embodiment (3), wherein $R^1$ is fluoro, and n is 1.

(5) The compound of embodiment (1), wherein the compound is of formula (III)

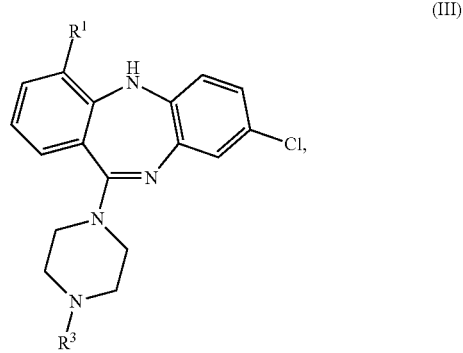

(III)

wherein $R^2$ is fluoro, bromo, or iodo, and $R^3$ is methyl or ethyl, or a pharmaceutically acceptable salt thereof.

(6) The compound of embodiment (1), wherein the compound is selected from the group consisting of

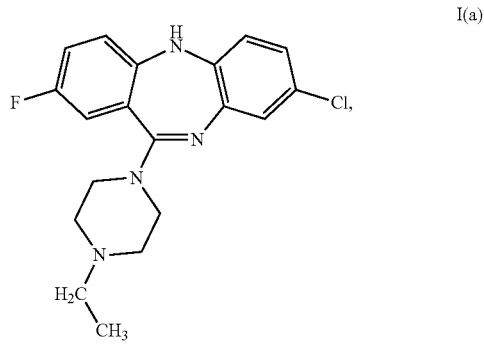

I(a)

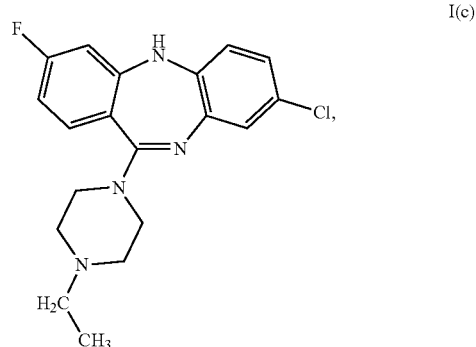

I(c)

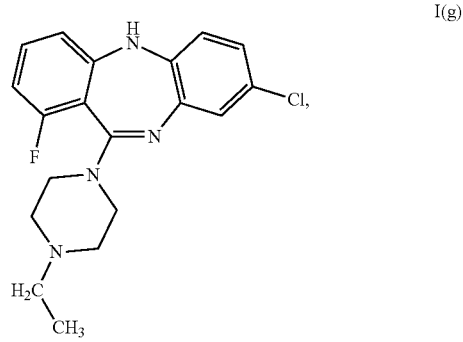

I(g)

-continued

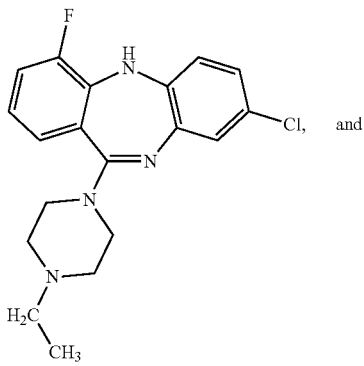

I(h)

or a pharmaceutically acceptable salt thereof.

(7) The compound of embodiment (6), wherein the compound is

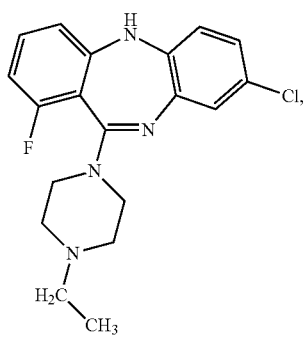

I(g)

or a pharmaceutically acceptable salt thereof.

(8) The compound of embodiment (6), wherein the compound is

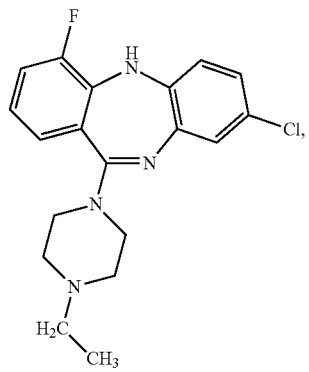

I(h)

or a pharmaceutically acceptable salt thereof.

(9) The compound of embodiment (1), wherein the compound is

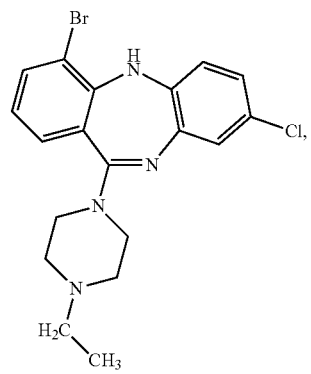

I(i)

or a pharmaceutically acceptable salt thereof.

(10) The compound of embodiment (9), wherein the bromo substituent is bromine-76 ($^{76}$B).

(11) The compound of embodiment (1), wherein the compound is

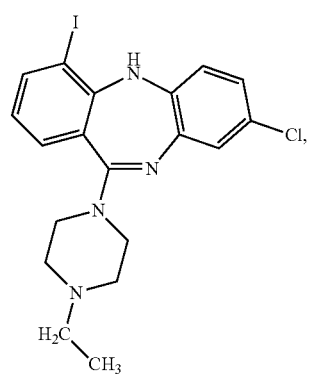

I(j)

or a pharmaceutically acceptable salt thereof.

(12) The compound of embodiment (11), wherein the iodo substituent is iodine-124 ($^{124}$I).

(13) The compound of embodiment (1), wherein the compound is of formula (V)

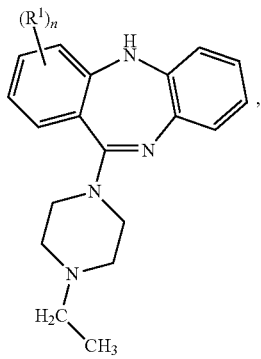

(V)

wherein R¹ is fluoro, and n is 1, or a pharmaceutically acceptable salt thereof.

(14) The compound of embodiment (13), wherein the compound is selected from the group consisting of

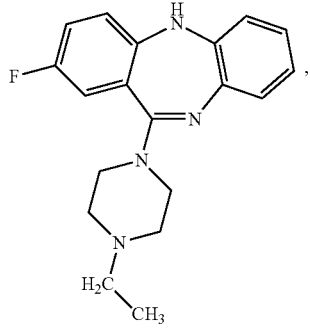

(I)b

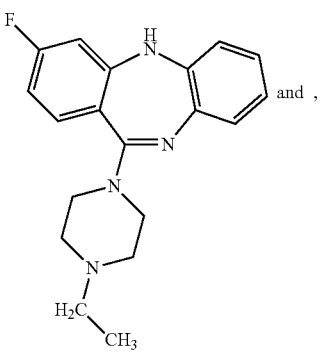

(I)d and,

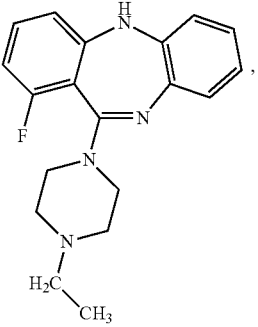

I(e)

or a pharmaceutically acceptable salt thereof.

(15) The compound of embodiment (1), wherein the compound is

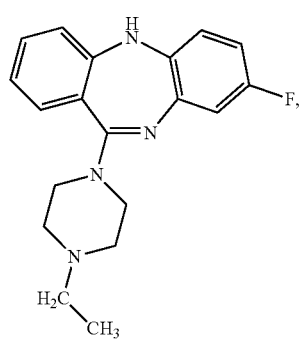

I(f)

or a pharmaceutically acceptable salt thereof.

(16) The compound of any one of embodiments (1)-(8) and (13)-(15), wherein the fluoro substituent is fluorine-18 ($^{18}$F).

(17) A pharmaceutical composition comprising a pharmaceutically acceptable carrier and a compound of any one of embodiments (1)-(16), or a pharmaceutically acceptable salt thereof.

(18) A method of treating a disease or disorder in a subject in need thereof comprising administering the compound of any one of embodiments (1)-(16), a pharmaceutically acceptable salt thereof, or the composition of embodiment (17), to the subject.

(19) The method of embodiment (18), wherein the disease or disorder is a disease or disorder of the brain.

(20) A method for effectuating a G-protein coupled receptor (GPCR)-mediated response in a subject, the method comprising:
administering to the subject a vector encoding a DREADD-modified human muscarinic GPCR (hM-DREADD), wherein the modified receptor is selected from the group consisting of hM3Dq and hM4Di, to express the modified receptor, and
administering the compound of any one of embodiments (1)-(9), (11), and (13)-(15), or a pharmaceutically acceptable salt thereof, to the subject.

(21) The method of embodiment (20), further comprising: administering the compound of any one of embodiments (10), (12), and (16), or a pharmaceutically acceptable salt thereof, to the subject, and imaging the subject by positron emission tomography.

(22) The method of embodiment (21), further comprising:
comparing the level of expression of the modified receptor as determined by positron emission tomography to a control, and
adjusting the amount of the compound of any one of embodiments (1)-(9), (11), and (13)-(15), or a pharmaceutically acceptable salt thereof, that is administered to the subject.

(23) The method of embodiment 20, further comprising:
imaging the subject by magnetic resonance imaging (MRI), and optionally magnetic resonance spectroscopy.

(24) The method of embodiment 23, further comprising:
comparing the level of expression of the modified receptor as determined by MRI to a control, and
adjusting the amount of the compound of any one of embodiments (1)-(9), (11), and (13)-(15), or a pharmaceutically acceptable salt thereof, that is administered to the subject.

The following examples further illustrate the invention but, of course, should not be construed as in any way limiting its scope.

EXAMPLES

Example 1

This example demonstrates suitable synthetic schemes for compounds of formula (I) in an embodiment of the invention.

All $^1$H NMR spectra were obtained with a 500 MHz spectrometer using CDCl$_3$ (7.27 ppm), as an internal reference. Signals are reported as m (multiplet), s (singlet), d (doublet), t (triplet), q (quartet), and bs (broad singlet); and coupling constants are reported in Hertz (Hz). $^{13}$C NMR spectra were obtained with a 125 MHz spectrometer using CDCl$_3$ (77.2 ppm) as the internal standard. High-resolution (positive ion) mass spectra (HRMS) were acquired using a LCMS (ESI) mass spectrometer.

Figure 20:
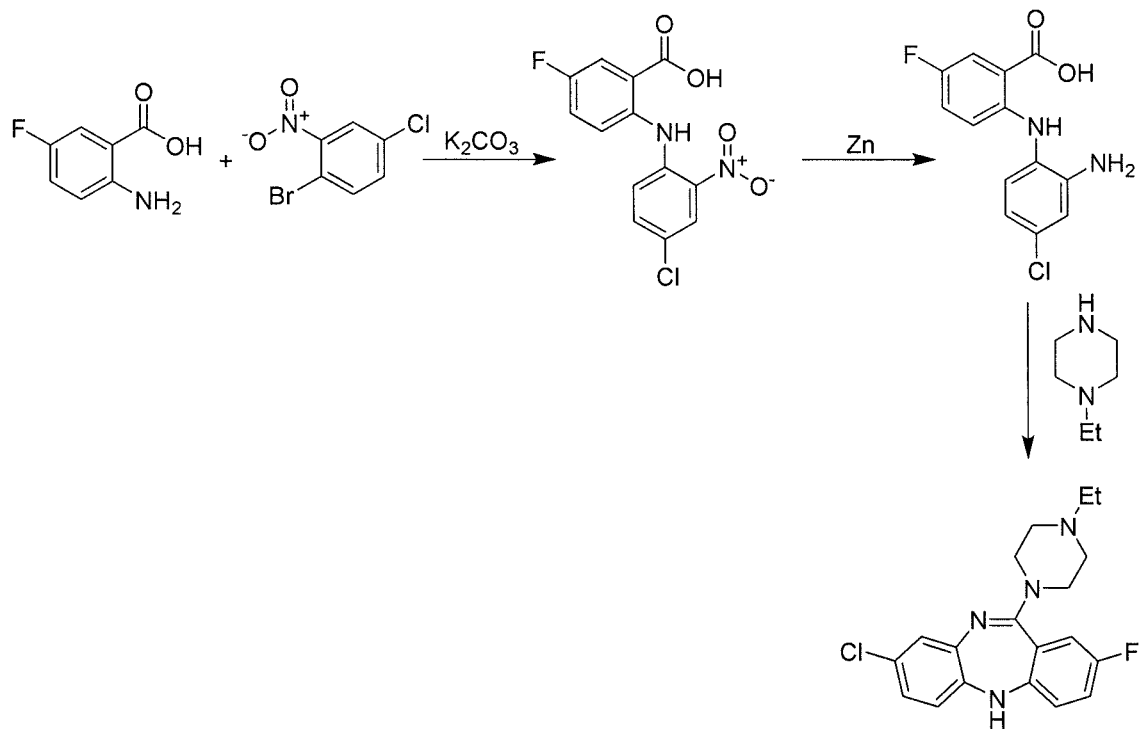
FIG. 20 depicts the synthesis of 8-chloro-11-(4-ethylpiperazin-1-yl)-2-fluoro-5H-dibenzo[b,e][1,4]diazepine (Compound I(a)) in accordance with an embodiment of the invention.

FIG. 20 shows the synthesis of 8-chloro-11-(4-ethylpiperazin-1-yl)-2-fluoro-5H-dibenzo[b,e][1,4]diazepine (Compound I(a) [JHU37107]) in an embodiment of the invention. This procedure is a general procedure which can be modified as needed to synthesize the compounds of an embodiment of the invention.

2-Amino-5-fluorobenzoic acid (4.96 g, 32 mmol) was treated with pentanol (50 mL), and the mixture was heated to 140° C. 1-Bromo-4-chloro-2-nitrobenzene (7.56 g, 32 mmol) was added to the reaction mixture, followed by K$_2$CO$_3$ (4.42 g, 32.00 mmol), and Cu powder (155 mg, 2.44 mmol). The mixture was refluxed for 6 hours. After cooling down, the precipitated solid was filtered and then dissolved in water, acidified with a dilute aqueous HCl solution to provide a yellow solid, which was dried under vacuum. The crude solid 2-((4-chloro-2-nitrophenyl)amino)-5-fluorobenzoic acid was used for the next step without further purification (8.93 g, 90% yield).

The above crude compound 2-((4-chloro-2-nitrophenyl)amino)-5-fluorobenzoic acid (0.5 g, 1.6 mmol) was treated with methanol (10 mL), NH$_4$Cl (0.46 g, 8 mmol), and Zn (0.52 g, 8 mmol) using an ice-bath. Then the mixture was stirred at room temperature for 2 hours, filtered to remove the solid, and the filtrate was concentrated under vacuum to provide a deep green solid. The solid was treated with dichloromethane (20 mL) and 1-(3-dimethylaminopropyl)-3-ethylcarbodiimide hydrochloride (EDC HC) (0.92 g, 4.8 mmol). The mixture was stirred at room temperature under argon for 12 hours, which then was concentrated to provide a pale residue. The residue was treated with TiCl$_4$ (1M in toluene) (1.9 mL, 1.9 mmol) and 1-ethylpiperazine (0.92 g, 8 mmol) in 1,4-dioxane (50 mL) under argon. The mixture was heated to 100° C. for 5 hours. After cooling, the mixture was acidified with 1M HCl aqueous solution and then extracted with EtOAc. The aqueous layer was basified with 1M NaOH aqueous solution, and then extracted with EtOAc. The organic layer was dried with Na$_2$SO$_4$, and concentrated for purification with a silica gel column to provide the pure product, compound I(a), as a yellow solid (0.145 g, 25% yield over three steps).

$^1$H NMR (500 MHz, CDCl$_3$) δ 7.08 (d, J=2.3 Hz, 1H), 7.03 (td, J=8.2, 2.9 Hz, 1H), 6.99 (dd, J=8.7, 2.9 Hz, 1H), 6.85 (dd, J=8.3, 2.4 Hz, 1H), 6.63 (d, J=8.3 Hz, 1H), 4.83 (s, 1H), 3.50 (bs, 4H), 2.56 (bs, 4H), 2.50 (dd, J=14.4, 7.3 Hz, 2H), 1.13 (t, J=7.2 Hz, 3H). HRMS (ESI+) calculated for C$_{19}$H$_{21}$ClFN$_4$ (M+H)$^+$: 359.1439; found: 359.1435.

11-(4-Ethylpiperazin-1-yl)-2-fluoro-5H-dibenzo[b,e][1,4]diazepine (Compound I(b) [JHU37120])

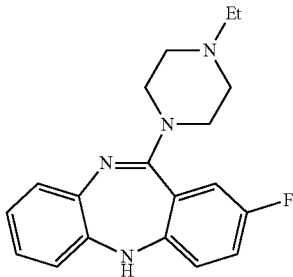 [SMILES: CCN1CCN(C2=Nc3ccccc3Nc3ccc(F)cc32)CC1]

According to the general procedure shown in FIG. 20, 2-amino-5-fluorobenzoic acid (4.96 g, 32 mmol) and 1-iodo-2-nitrobenzene (7.97 g, 32 mmol) were used. The crude compound 5-fluoro-2-((2-nitrophenyl)amino)benzoic acid was obtained (6.35 g, 71.9% yield).

The above crude compound 5-fluoro-2-((2-nitrophenyl)amino)benzoic acid (1.6 mmol) was used to provide the product, compound I(b), as a yellow solid (0.144 g, 27.5% yield over three steps).

$^1$H NMR (500 MHz, CDCl$_3$) δ 7.12-7.07 (m, 1H), 7.04-6.97 (m, 3H), 6.90 (td, J=7.6, 1.4 Hz, 1H), 6.79 (dd, J=9.4, 4.7 Hz, 1H), 6.74-6.69 (m, 1H), 4.86 (s, 1H), 3.49 (bs, 4H), 2.57 (bs, 4H), 2.50 (q, J=7.2 Hz, 2H), 1.13 (t, J=7.2 Hz, 3H). HRMS (ESI+) calculated for C$_{19}$H$_{22}$FN$_4$ (M+H)$^+$: 325.1828; found: 325.1819.

8-Chloro-11-(4-ethylpiperazin-1-yl)-3-fluoro-5H-dibenzo[b,e][1,4]diazepine (Compound I(c) [JHU37127])

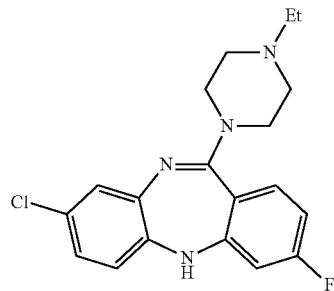 [SMILES: CCN1CCN(C2=Nc3cc(Cl)ccc3Nc3cc(F)ccc32)CC1]

According to the general procedure shown in FIG. 20, 2-amino-4-fluorobenzoic acid (4.96 g, 32 mmol) and 1-bromo-4-chloro-2-nitrobenzene (7.56 g, 32 mmol) were used. The crude compound 2-((4-chloro-2-nitrophenyl)amino)-4-fluorobenzoic acid was obtained (7.86 g, 79.2% yield).

The crude compound I(b) (1.6 mmol) was used to provide the product, compound I(c), as a yellow solid (0.165 g, 28.8% yield over three steps).

$^1$H NMR (500 MHz, CDCl$_3$) δ 7.27-7.23 (m, 1H), 7.07 (d, J=2.3 Hz, 1H), 6.84 (dd, J=8.3, 2.4 Hz, 1H), 6.74 (td, J=8.4, 2.4 Hz, 1H), 6.61 (d, J=8.3 Hz, 1H), 6.57 (dd, J=9.2, 2.4 Hz, 1H), 4.91 (s, 1H), 3.47 (bs, 4H), 2.55 (bs, 4H), 2.49 (dd, J=14.4, 7.2 Hz, 3H), 2.49 (dd, J=14.4, 7.2 Hz, 3H). HRMS (ESI+) calculated for calculated for C$_{19}$H$_{21}$ClFN$_4$ (M+H)$^+$: 359.1456; found: 359.1435.

11-(4-Ethylpiperazin-1-yl)-3-fluoro-5H-dibenzo[b,e][1,4]diazepine (Compound I(d) [JHU37130])

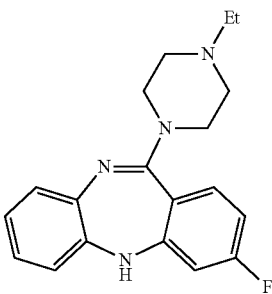 [SMILES: CCN1CCN(C2=Nc3ccccc3Nc3cc(F)ccc32)CC1]

According to the general procedure shown in FIG. 20, 2-amino-4-fluorobenzoic acid (4.96 g, 32 mmol) and 1-iodo-2-nitrobenzene (7.97 g, 32 mmol) were used. The crude compound 4-fluoro-2-((2-nitrophenyl)amino)benzoic acid was obtained (6.68 g, 75.6% yield).

The above crude compound 4-fluoro-2-((2-nitrophenyl)amino)benzoic acid (1.6 mmol) was used to provide the product, compound I(d), as a yellow solid (0.189 g, 36.1% yield over three steps).

$^1$H NMR (500 MHz, CDCl$_3$) δ 7.30-7.24 (m, 1H), 7.09 (d, J=7.7 Hz, 1H), 7.00 (t, J=7.6 Hz, 1H), 6.90 (t, J=7.4 Hz, 1H), 6.73-6.68 (m, 2H), 6.57 (d, J=9.2 Hz, 1H), 4.95 (s, 1H), 3.46 (bs, 4H), 2.56 (bs, 4H), 2.49 (dd, J=14.4, 7.2 Hz, 2H), 1.13 (t, J=7.1 Hz, 3H). HRMS (ESI+) calculated for C$_{19}$H$_{22}$FN$_4$ (M+H)$^+$: 325.1828; found: 325.1822.

8-Chloro-11-(4-ethylpiperazin-1-yl)-1-fluoro-5H-dibenzo[b,e][1,4]diazepine (Compound I(g) [JHU37152])

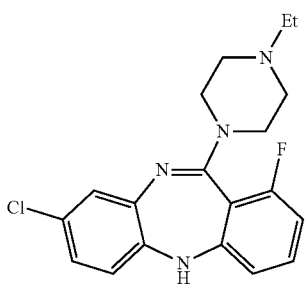 [SMILES: CCN1CCN(C2=Nc3cc(Cl)ccc3Nc3cccc(F)c32)CC1]

According to the general procedure shown in FIG. 20, 2-amino-6-fluorobenzoic acid (2.48 g, 16 mmol) and 4-chloro-1-iodo-2-nitrobenzene (4.53 g, 16 mmol) were used. The crude compound 2-((4-chloro-2-nitrophenyl)amino)-6-fluorobenzoic acid was obtained (4.89 g, 98.4% yield).

The above crude compound 2-((4-chloro-2-nitrophenyl)amino)-6-fluorobenzoic acid (1.6 mmol) was used and in the last step, anisole (50 mL) as a solvent instead of 1,4-dioxane at 130° C. for 1 h to provide the product, compound I(g), as a yellow solid (0.225 g, 39.4% yield over three steps).

$^1$H NMR (500 MHz, CDCl$_3$) δ 7.28-7.23 (m, 1H), 7.06 (s, 1H), 6.79 (d, J=8.3 Hz, 1H), 6.76 (t, J=9.0 Hz, 1H), 6.67 (d, J=7.9 Hz, 1H), 6.62 (d, J=8.3 Hz, 1H), 4.95 (s, 1H), 3.59 (bs, 4H), 2.59 (bs, 1H), 2.48 (d, J=7.0 Hz, 2H), 1.13 (t, J=7.2 Hz, 3H). HRMS (ESI+) calculated for calculated for C$_{19}$H$_{21}$ClFN$_4$ (M+H)$^+$: 359.1456; found: 359.1435.

11-(4-Ethylpiperazin-1-yl)-1-fluoro-5H-dibenzo[b,e][1,4]diazepine (Compound I(e) [JHU37140])

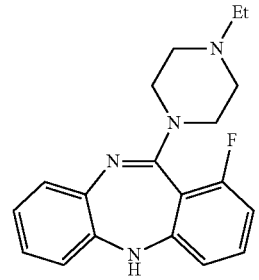 [SMILES: CCN1CCN(C2=Nc3ccccc3Nc3cccc(F)c32)CC1]

According to the general procedure shown in FIG. 20, 2-amino-6-fluorobenzoic acid (4.96 g, 32 mmol) and 1-iodo-2-nitrobenzene (7.97 g, 32 mmol) were used. The crude compound 6-fluoro-2-((2-nitrophenyl)amino)benzoic acid was obtained (7.36 g, 83.3% yield).

The above crude compound 6-fluoro-2-((2-nitrophenyl)amino)benzoic acid (1.6 mmol) was used to provide the product, compound I(e), as a yellow solid (0.131 g, 25.3% yield over three steps).

$^1$H NMR (500 MHz, CDCl$_3$) δ 7.22 (dd, J=14.5, 7.5 Hz, 1H), 7.08 (d, J=7.8 Hz, 1H), 6.99 (t, J=7.5 Hz, 1H), 6.85 (t, J=7.5 Hz, 1H), 6.72 (t, J=8.3 Hz, 2H), 6.67 (d, J=7.9 Hz, 1H), 5.02 (s, 1H), 3.55 (s, 4H), 2.60 (s, 2H), 2.53-2.46 (m, 4H), 1.12 (t, J=7.1 Hz, 3H). HRMS (ESI+) calculated for C$_9$H$_{22}$FN$_4$ (M+H)$^+$: 325.1828; found: 325.1810.

8-Chloro-11-(4-ethylpiperazin-1-yl)-4-fluoro-5H-dibenzo[b,e][1,4]diazepine (Compound I(h) [JHU37160])

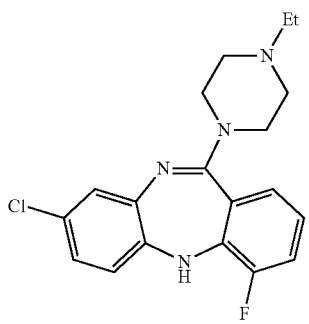 [SMILES: CCN1CCN(C2=Nc3cc(Cl)ccc3Nc3c(F)cccc32)CC1]

According to the general procedure shown in FIG. 20, 2-amino-3-fluorobenzoic acid (2.48 g, 16 mmol) and 4-chloro-1-iodo-2-nitrobenzene (4.53 g, 16 mmol) were used. The crude compound 2-((4-chloro-2-nitrophenyl)amino)-3-fluorobenzoic acid was obtained (4.91 g, 98.6% yield).

The above crude compound 2-((4-chloro-2-nitrophenyl)amino)-3-fluorobenzoic acid (1.6 mmol) was used to provide the product, compound I(h), as a yellow solid (0.265 g, 44.9% yield over three steps).

$^1$H NMR (500 MHz, CDCl$_3$) δ 7.15-7.09 (m, 1H), 7.07 (d, J=2.3 Hz, 1H), 7.05 (d, J=7.8 Hz, 1H), 6.95 (td, J=8.0, 5.1 Hz, 1H), 6.85 (dd, J=8.3, 2.4 Hz, 1H), 6.68 (d, J=8.3 Hz, 1H), 5.34 (d, J=3.8 Hz, 1H), 3.49 (bs, 4H), 2.55 (bs, 3H), 2.49 (q, J=7.2 Hz, 2H), 1.13 (t, J=7.2 Hz, 3H). HRMS (ESI+) calculated for calculated for C$_9$H$_{21}$ClFN$_4$ (M+H)$^+$: 359.1456; found: 359.1435.

11-(4-Ethylpiperazin-1-yl)-8-fluoro-5H-dibenzo[b,e][1,4]diazepine (Compound I(f) [JHU37146])

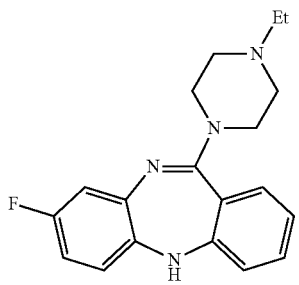 [SMILES: CCN1CCN(C2=Nc3cc(F)ccc3Nc3ccccc32)CC1]

According to the general procedure shown in FIG. 20, 2-aminobenzoic acid (4.39 g, 32 mmol) and 4-fluoro-1-iodo-2-nitrobenzene (8.54 g, 32 mmol) were used. The crude compound 2-((4-fluoro-2-nitrophenyl)amino)benzoic acid was obtained (8.54 g, 96.6% yield).

The above crude compound 2-((4-fluoro-2-nitrophenyl)amino)benzoic acid (1.6 mmol) was used to provide the product, compound I(f), as a yellow solid (0.289 g, 55.7% yield over three steps).

$^1$H NMR (500 MHz, CDCl$_3$) δ 7.34-7.27 (m, 2H), 7.02 (t, J=7.4 Hz, 1H), 6.84 (d, J=7.7 Hz, 1H), 6.79 (d, J=10.1 Hz, 1H), 6.67-6.60 (m, 1H), 6.57 (t, J=8.2 Hz, 1H), 4.87 (s, 1H), 3.51 (bs, 4H), 2.56 (bs, 4H), 2.50 (q, J=6.6 Hz, 2H), 1.14 (t, J=7.0 Hz, 3H). HRMS (ESI+) calculated for C$_{19}$H$_{22}$FN$_4$ (M+H)$^+$: 325.1828; found: 325.1847.

4-Bromo-8-chloro-11-(4-ethylpiperazin-1-yl)-5H-dibenzo[b,e][1,4]diazepine (Compound I(i) [JHU371104])

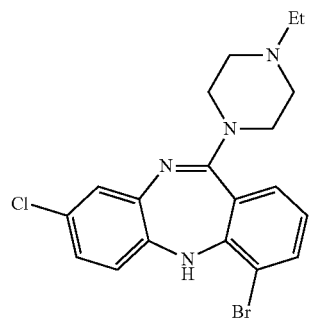 [SMILES: CCN1CCN(C2=Nc3cc(Cl)ccc3Nc3c(Br)cccc32)CC1]

Figure 24:
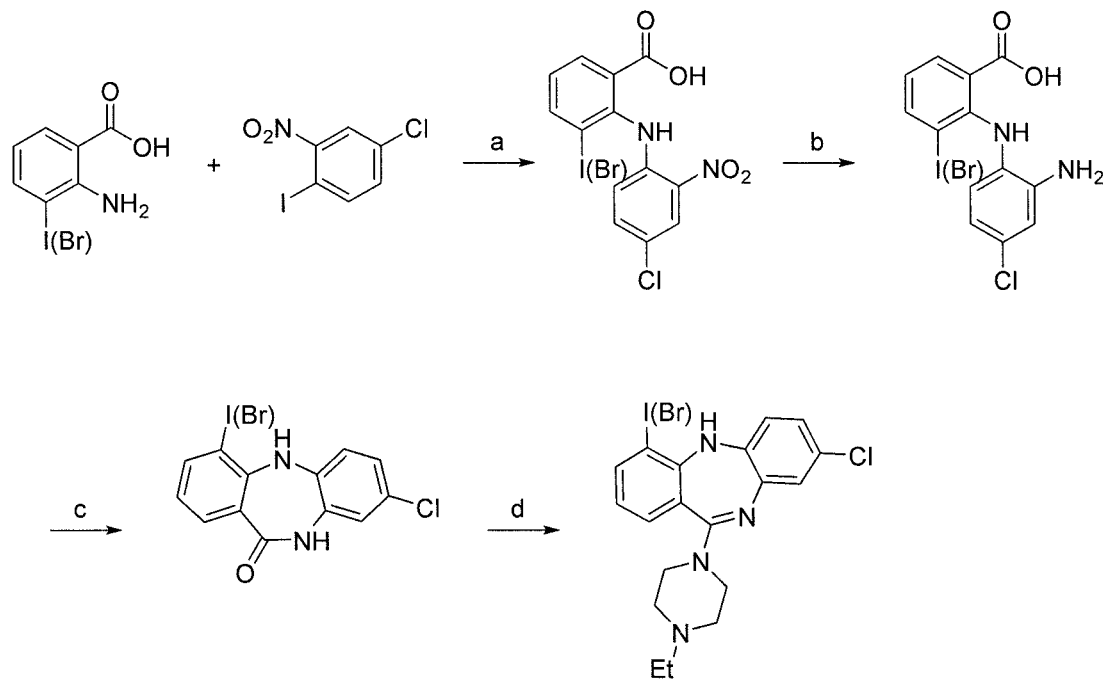
FIG. 24 depicts the synthesis of 4-bromo-8-chloro-11-(4-ethylpiperazin-1-yl)-5H-dibenzo[b,e][1,4]diazepine Compound I(i) and 8-chloro-11-(4-ethylpiperazin-1-yl)-4-iodo- 5H-dibenzo[b,e][1,4]diazepine Compound I(j) in accordance with an embodiment of the invention. "I(Br)" in FIG. 24 means that I or Br can be present at that position in the compounds.

FIG. 24 shows the synthesis of 4-bromo-8-chloro-11-(4-ethylpiperazin-1-yl)-5H-dibenzo[b,e][1,4]diazepine in an embodiment of the invention. This procedure is a general procedure which can be modified as needed to synthesize Br- and I-containing compounds in an embodiment of the invention. "I(Br)" in FIG. 24 means that I or Br can be present at that position in the compounds. For example, Br is present in that position for the synthesis of Compound I(i).

The following reagents and conditions were used in the synthesis depicted in FIG. 24: (a) K$_2$CO$_3$, dimethylformamide (DMF), 140° C.; (b) Fe, NH$_4$Cl, EtOH/H$_2$O, 65° C.; (c) N'-ethylcarbodiimide hydrochloride (EDC HCl), CH$_2$Cl$_2$, room temperature; and (d) TiCl$_4$, 1,4-dioxane, 1-ethylpiperazine, reflux.

2-amino-3-bromobenzoic acid (0.432 g, 2 mmol) and 4-fluoro-1-iodo-2-nitrobenzene (0.477 g, 2 mmol) were used. The crude compound 3-bromo-2-((4-chloro-2-nitrophenyl)amino)benzoic acid was obtained (0.668 g, 90.1% yield).

The above crude compound 3-bromo-2-((4-chloro-2-nitrophenyl)amino)benzoic acid (1.6 mmol) was used to provide the product, compound I(i), as a yellow solid (0.176 g, 26.3% yield over three steps).

$^1$H NMR (400 MHz, CDCl$_3$) δ 7.58 (dd, J=7.7, 1.3 Hz, 1H), 7.23 (dd, J=7.7, 1.0 Hz, 1H), 7.08 (s, 1H), 6.87 (d, J=1.6 Hz, 2H), 6.78 (t, J=7.8 Hz, 1H), 5.75 (s, 1H), 3.51 (bs, 4H), 2.56 (bs, 4H), 2.51 (dd, J=14.4, 7.2 Hz, 2H), 1.15 (t, J=7.2 Hz, 3H). HRMS (ESI+) calculated for C$_{19}$H$_{21}$ClBrN$_4$ (M+H)$^+$: 419.0638; found: 419.0628.

8-Chloro-11-(4-ethylpiperazin-1-yl)-4-iodo-5H-dibenzo[b,e][1,4]diazepine (Compound I(j) [JHU371112])

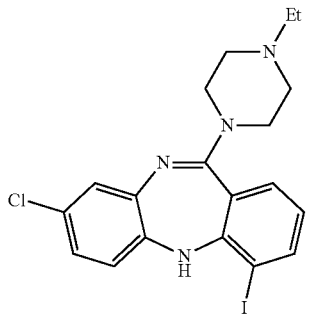 [SMILES: CCN1CCN(C2=Nc3cc(Cl)ccc3Nc3c(I)cccc32)CC1]

According to the general procedure of FIG. 24, 2-amino-3-iodobenzoic acid (0.526 g, 2 mmol) and 4-fluoro-1-iodo-2-nitrobenzene (0.477 g, 2 mmol) were used. The crude compound 2-((4-chloro-2-nitrophenyl)amino)-3-iodobenzoic acid was obtained (0.789 g, 94.0% yield).

The above crude compound 3-bromo-2-((4-chloro-2-nitrophenyl)amino)benzoic acid (1.6 mmol) was used to provide the product, compound I(j), as a yellow solid (0.193 g, 25.8% yield over three steps).

$^1$H NMR (500 MHz, CDCl$_3$) δ 7.80 (dd, J=7.8, 1.3 Hz, 1H), 7.23 (dd, J=7.7, 1.0 Hz, 1H), 7.08 (s, 1H), 6.87 (d, J=1.6 Hz, 2H), 6.75 (t, J=7.8 Hz, 1H), 5.57 (s, 1H), 3.56 (bs, 4H), 2.62 (bs, 4H), 2.57 (dd, J=14.4, 7.2 Hz, 2H), 1.17 (t, J=7.2 Hz, 3H). HRMS (ESI+) calculated for C$_{19}$H$_{21}$ClIN$_4$ (M+H)$^+$: 467.0499; found: 467.0491.

8-Chloro-4-fluoro-11-(4-methylpiperazin-1-yl)-5H-dibenzo[b,e][1,4]diazepine (Compound I(k) [JHU371148])

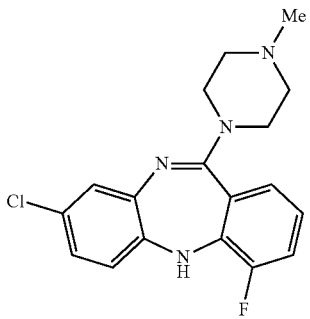 [SMILES: CN1CCN(C2=Nc3cc(Cl)ccc3Nc3c(F)cccc32)CC1]

According to the general procedure above, 2-amino-3-fluorobenzoic acid (2.48 g, 16 mmol) and 4-chloro-1-iodo-2-nitrobenzene (4.53 g, 16 mmol) were used. The crude compound 2-((4-chloro-2-nitrophenyl)amino)-3-fluorobenzoic acid was obtained (4.91 g, 98.6% yield).

The above crude compound 2-((4-chloro-2-nitrophenyl)amino)-3-fluorobenzoic acid (1.6 mmol) was used to provide the product, compound I(k), as a yellow solid (0.105 g, 19.1% yield over three steps).

$^1$H NMR (400 MHz, CDCl$_3$) δ 7.13 (ddd, J=9.6, 8.1, 1.4 Hz, 1H), 7.07 (d, J=2.4 Hz, 1H), 7.06 (d, J=8.1 Hz, 1H), 6.96 (td, J=8.0, 5.1 Hz, 1H), 6.86 (dd, J=8.3, 2.4 Hz, 1H), 6.69 (d, J=8.3 Hz, 1H), 5.34 (d, J=3.9 Hz, 1H), 3.49 (s, 4H), 3.49 (s, 4H), 2.36 (s, 3H). HRMS (ESI+) calculated for C$_8$H$_{19}$CFN$_4$ (M+H)$^+$: 345.1282; found: 345.1281.

Figure 21:
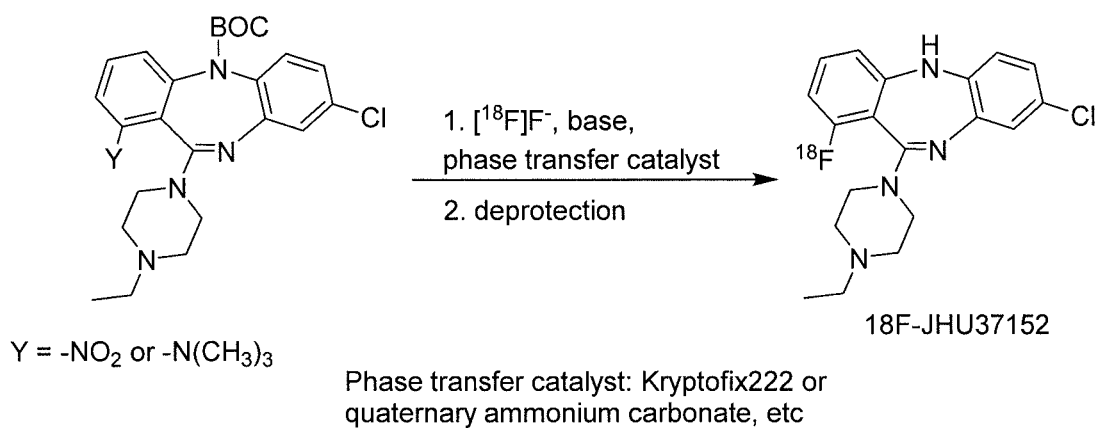
FIG. 21 depicts the synthesis of 8-chloro-11-(4-ethylpiperazin-1-yl)-1-fluoro($^{18}$F)-5H-dibenzo[b,e][1,4]diazepine (Compound [$^{18}$F]I(g)) in accordance with an embodiment of the invention.

8-Chloro-11-(4-ethylpiperazin-1-yl)-1-fluoro($^{18}$F)-5H-dibenzo[b,e][1,4]diazepine (Compound [$^{18}$F]I(g) [$^{18}$F JHU37152]) may be synthesized according to the procedure of FIG. 21.

Figure 22:
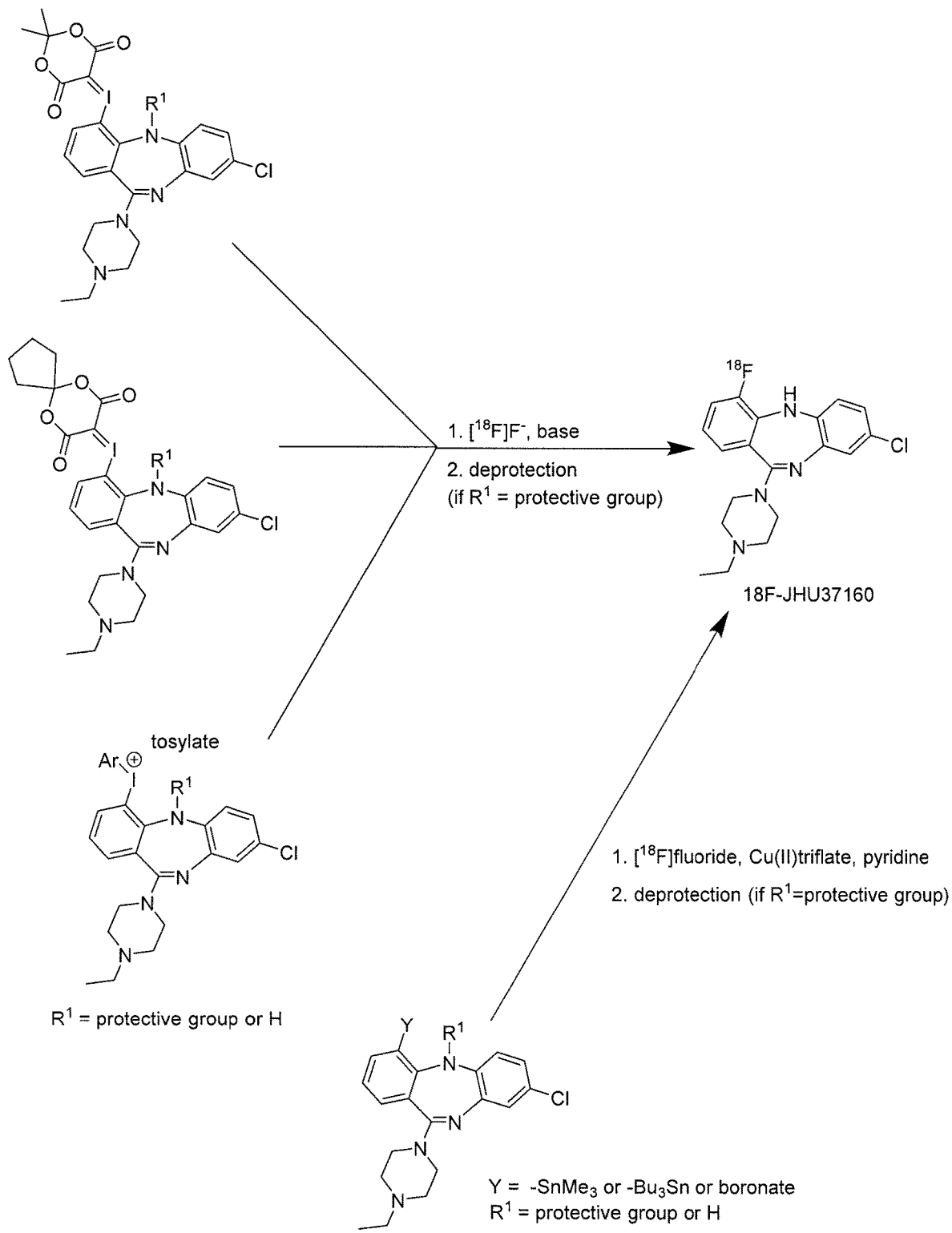
FIG. 22 depicts the synthesis of 8-chloro-11-(4-ethylpiperazin-1-yl)-4-fluoro($^{18}$F)-5H-dibenzo[b,e][1,4]diazepine (Compound [$^{18}$F]I(h)) in accordance with an embodiment of the invention.

8-Chloro-11-(4-ethylpiperazin-1-yl)-4-fluoro($^{18}$F)-5H-dibenzo[b,e][1,4]diazepine (Compound [$^{18}$F]I(h) [$^{18}$F JHU37160]) may be synthesized according to the procedure of FIG. 22.

Figure 25:
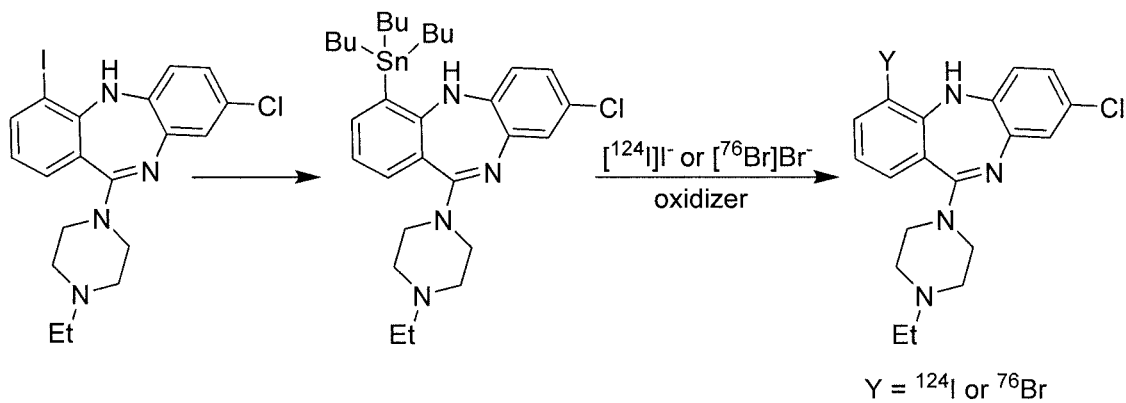
FIG. 25 depicts the synthesis of Compound [$^{76}$Br]I(i) and Compound [$^{124}$I]I(j) in accordance with an embodiment of the invention.

4-Bromo($^{76}$Br)-8-chloro-11-(4-ethylpiperazin-1-yl)-5H-dibenzo[b,e][1,4]diazepine (Compound [$^{76}$Br]I(i) [$^{76}$Br JHU371104]) and 8-chloro-11-(4-ethylpiperazin-1-yl)-4-iodo($^{124}$I)-5H-dibenzo[b,e][1,4]diazepine (Compound [$^{124}$I](j) [$^{124}$I JHU371112]) may e synthesized according to the procedure set forth in FIG. 25.

Example 2

This example describes a radioligand binding assay that demonstrates that compounds of formula (I) are effective at binding hM3Dq and hM4Di.

HEK-293 cells were transfected with 5 μg/dish of pAAV plasmids encoding for hM3Dq (available from Addgene, Cambridge, Mass., plasmid #89149), hM4Di (available from Addgene, Cambridge, Mass., plasmid #89150) or a control vector and harvested 48 hours after transfection. Cells were suspended in Tris-HCl 50 mM (pH 7.4) supplemented with a protease inhibitor cocktail (1:100) and disrupted with a homogenizer. Homogenates were centrifuged at 48,000 g (50 min, 4° C.) and washed 2 times in the same conditions to isolate the membrane fraction. The protein was quantified by the bicinchoninic acid method. Membrane suspensions (50 μg of protein/ml) were incubated in 50 mM Tris-HCl (pH 7.4) containing 10 mM MgCl$_2$, 2.5 nM of [$^3$H]clozapine and increasing concentrations of test ligands during 2 hours at room temperature. In all cases, free and membrane-bound radioligand were separated by rapid filtration of 500-1 aliquots in a 96-well plate harvester and washed with 2 ml of ice-cold Tris-HCl buffer. Microscint-20 scintillation liquid (65 l/well) was added to the filter plates, plates were incubated overnight at room temperature and radioactivity counts were determined in a MICROBETA$^{2TM}$ (PerkinElmer, Waltham, Mass.) plate counter with an efficiency of 41%. Competition curves were fitted to a one binding site model and K$_i$ values were calculated using the Cheng-Prusoff equation.

TABLE 1

| | K$_i$ values (nM) | |
|---|---|---|
| Compound | hM3Dq | hM4Di |
| I(a) [JHU37107] | 10.5 | 23.5 |
| I(b) [JHU37120] | 33.45 | 118 |
| I(c) [JHU37127] | 51.4 | 51.3 |
| I(d) [JHU37130] | 101 | 149 |
| I(e) [JHU37140] | 4.8 | 14.2 |
| I(f) [JHU37146] | 23.7 | 12.9 |
| I(g) [JHU37152] | 1.7 | 8.7 |
| I(h) [JHU37160] | 1.9 | 3.6 |

Figure 2:
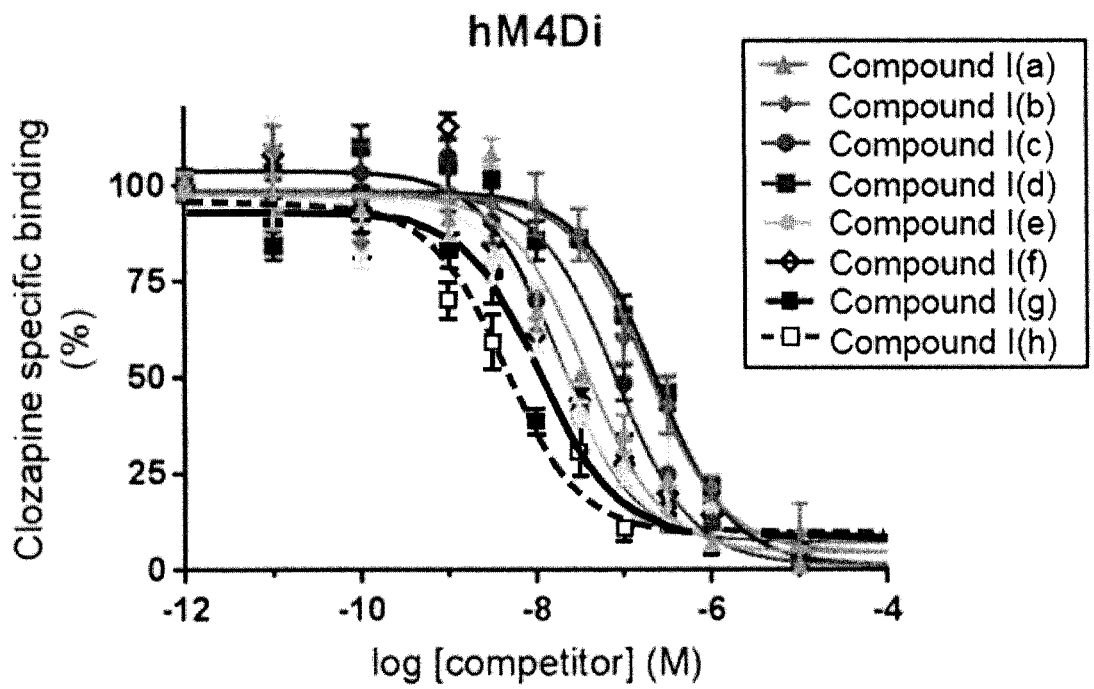
FIG. 2 is a graph showing the binding affinity of Compounds I(a)-I(h) to hM4Di receptor as compared to clozapine's specific binding to hM4Di receptor.

As seen in Table 1 above, FIG. 1, and FIG. 2, the compounds of formula (I) are effective at binding the tested DREADDs. Compounds I(g) and I(h) are especially effective at binding the tested DREADDs (low values being desirable).

Example 3

This example describes an autoradiography assay which demonstrates that compound I(h) displaces [$^3$H]clozapine binding to DREADDs, but not to endogenous sites, in brain sections from wild-type and transgenic DREADD mice.

Flash frozen brain tissue was sectioned (20 μm) on a cryostat and thaw mounted onto ethanol-washed glass slides. The slides were pre-incubated (10 mins at room temperature) in incubation buffer (170 mM Tris-HCl, 120 mM NaCl, 1 mM CaCl$_2$, pH 7.4) and then the slides were incubated for 60 mins in an incubation buffer containing about 3.5 nM [$^3$H]clozapine with or without increasing amounts of clozapine or compound I(h). Following incubation, the slides were washed with an incubation buffer for 5 mins (2×) followed by a 30 second dip in ice-cold deionized H$_2$O. The slides were then air-dried, placed in a HYPER-CASSETTE™ (GE Healthcare, UK) autoradiography cassette, covered with a BAS-TR2025 Storage Phosphor Screen (GE Healthcare, UK), exposed for 3-5 days, and imaged using a phosphorimager.

Figure 3:
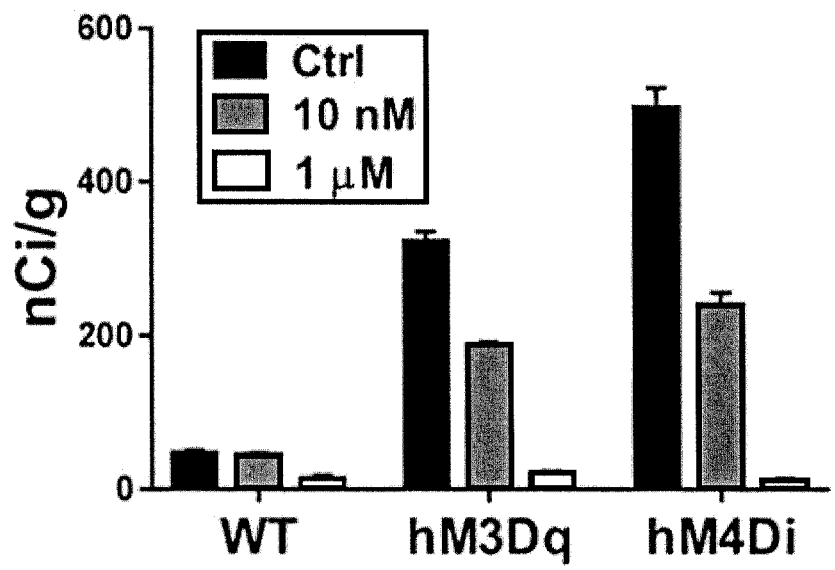
FIG. 3 is a graph showing the level of radioactivity from tissues exposed to [$^3$H]clozapine alone ("Ctrl") or in combination with compound I(h) at two different concentrations. The number of nanoCuries per gram ("nCi/g") is on the y-axis and the type of tissue, either wild type (labeled "WT" in graph) or transgenic mice tissue (with receptors hM3Dq or hM4Di), is on the x-axis.
Figure 4:
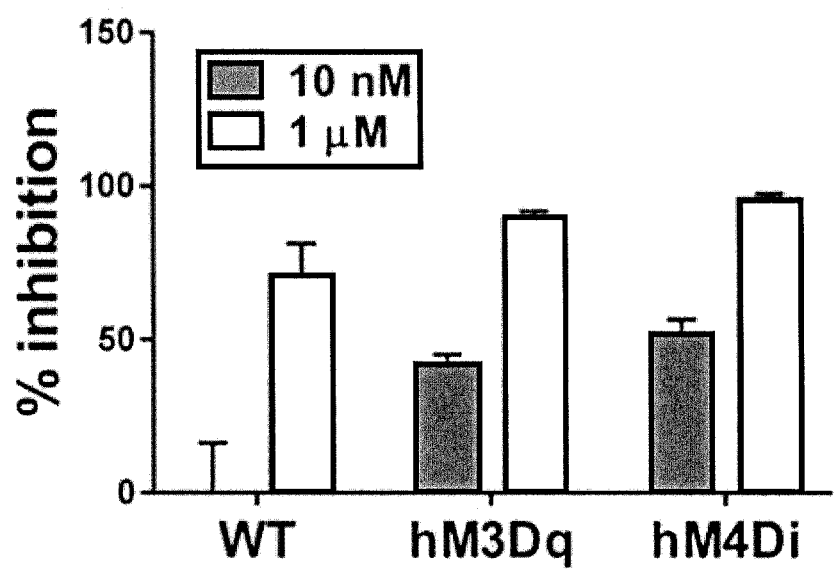
FIG. 4 is a graph showing the level of inhibition of [$^3$H]clozapine binding when tissues are exposed to compound I(h). The percent inhibition is on the y-axis and the type of tissue, either wild type (labeled "WT" in graph) or transgenic mice tissue (with receptors hM3Dq or hM4Di), is on the x-axis.

As seen in FIG. 3 and FIG. 4, at 10 nM, compound I(h) selectively displaced [$^3$H]clozapine binding to DREADDs but not to endogenous sites. At 1 μM, compound I(h) completely displaced [$^3$H]clozapine binding to both DREADDs and endogenous clozapine-binding sites.

Example 4

This example describes an in vitro functional assay which demonstrates that compound I(g) and compound I(h) are effective at activating Gi/o protein.

Bioluminescence resonance energy transfer ("BRET") assays were performed to detect receptor ligand-induced Gi/o protein activation. HEK-293 cells were transfected with 5 μg/dish of pAAV plasmids encoding for hM3Dq (available from Addgene, plasmid #89149), hM4Di (available from Addgene, plasmid #89150) or a control vector together with 0.5 μg Gα-Rluc8, 4.5 μg β1 and 5 μg γ2-mVenus/dish. Forty-eight hours after transfection cells were harvested, washed and resuspended in phosphate-buffered saline ("PBS"). Approximately 200,000 cells/well were distributed in 96-well plates, and 5 μM Coelenterazine H (substrate for luciferase) was added to each well. Five minutes after addition of Coelenterazine H, clozapine, CNO, compound 13, compound 21, compound I(g), or compound I(h) was added to the appropriate wells. Compound 13 has the following structure:

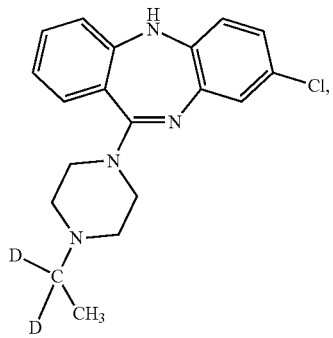 [SMILES: [2H]C([2H])(C)N1CCN(C2=Nc3cc(Cl)ccc3Nc3ccccc32)CC1]

and compound 21 has the following structure:

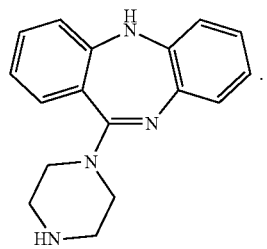 [SMILES: c1ccc2c(c1)N=C(N1CCNCC1)c1ccccc1N2]

The fluorescence of the acceptor was quantified (excitation at 500 nm and emission at 540 nm for 1-second recordings) in a PheraStar FSX plate reader (BMG Labtech, Ortenberg, Germany) to confirm the constant expression levels across experiments. In parallel, the BRET signal from the same batch of cells was determined as the ratio of the light emitted by mVenus (510-540 nm) over that emitted by RLuc (485 nm). Results were calculated for the BRET change (BRET ratio for the corresponding compound minus BRET ratio in the absence of the compound) 5 minutes after the addition of the compounds.

For the calcium accumulation assays, HEK293 cells were transfected with 7 μg/dish of pAAV plasmids encoding for hM3Dq (available from Addgene, plasmid #89149), hM4Di (available from Addgene, plasmid #89150) or a control vector and 7 μg of the fluorescence-based biosensor GCaMP6f. Forty-eight hours after transfection, the cells were resuspended in 150 uL of Locke buffer, seeded in 96-well block plates, and activated with increasing doses of clozapine, CNO, compound 13, compound 21, compound I(g), or compound I(h). The changes in fluorescence were read every 18 seconds for 5 minutes.

Figure 5:
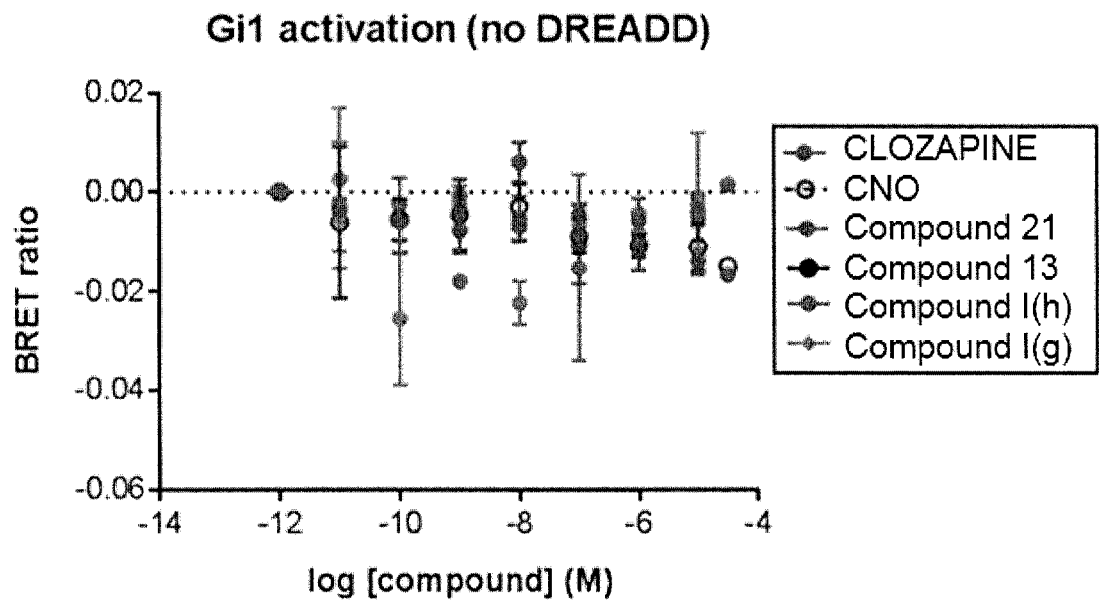
FIG. 5 is a graph showing the bioluminescence resonance energy transfer ratio ("BRET") of Gi1 activation of clozapine, CNO, compound 13, compound 21, compound I(g), and compound I(h) on cells without DREADD receptors.
Figure 6:
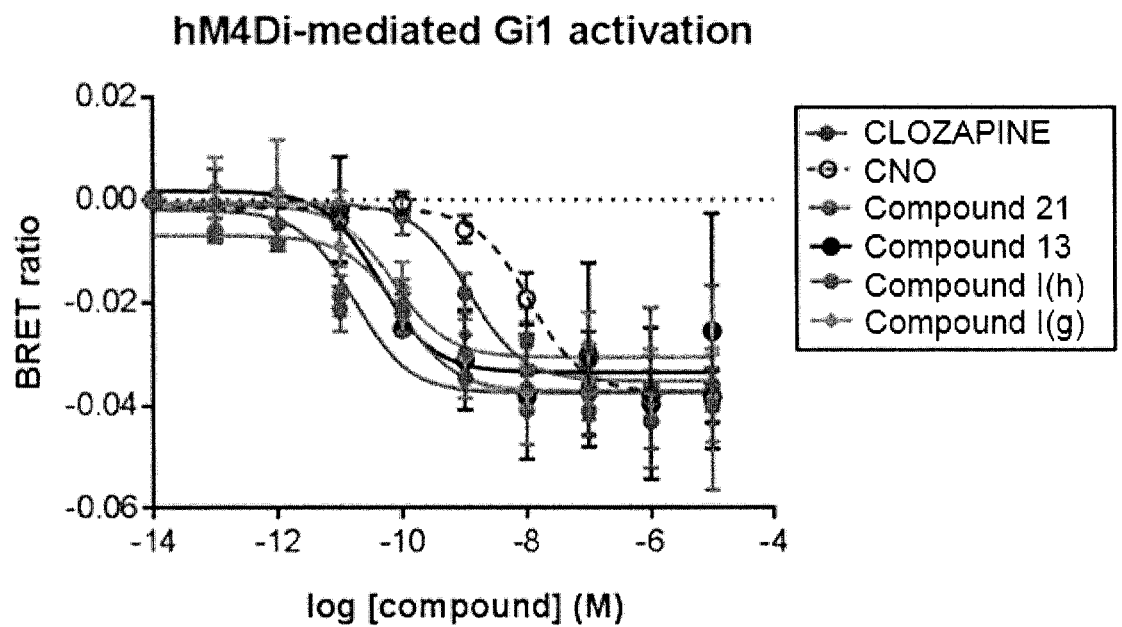
FIG. 6 is a graph showing the BRET of Gi1 activation of clozapine, CNO, compound 13, compound 21, compound I(g), and compound I(h) on cells with hM4Di receptors.

FIG. 5 shows the BRET ratio of Gi1 (a type of G protein) activation of clozapine, CNO, compound 13, compound 21, compound I(g), and I(h) on cells without DREADDs. FIG. 6 shows the BRET ratio of Gi1 activation of clozapine, CNO, compound 13, compound 21, compound I(g), and compound I(h) on cells with hM4Di. Comparing FIG. 5 with FIG. 6 (and evaluating Table 2) reveals that compound I(g) and compound I(h) activate Gi1.

TABLE 2

| EC$_{50}$ value summary (in M) for hM4Di (Gi1) | | |
|---|---|---|
| | mean | SEM |
| Clozapine | 1.90E−10 | 8.70E−11 |
| CNO | 1.30E−08 | 4.50E−09 |
| Compound 21 | 2.70E−09 | 1.00E−09 |
| Compound 13 | 6.70E−11 | 3.90E−11 |
| Compound I(g) [JHU37152] | 2.40E−10 | 1.40E−10 |
| Compound I(h) [JHU37160] | 7.30E−11 | 3.70E−11 |

Figure 7:
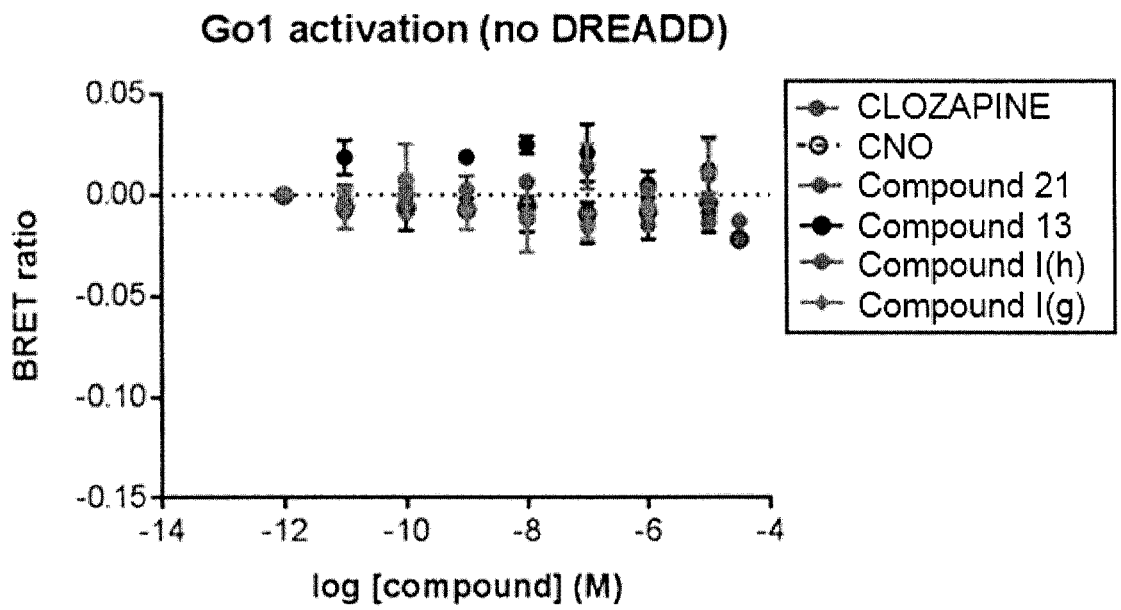
FIG. 7 is a graph showing the BRET of Go1 activation of clozapine, CNO, compound 13, compound 21, compound I(g), and compound I(h) on cells without DREADD receptors.
Figure 8:
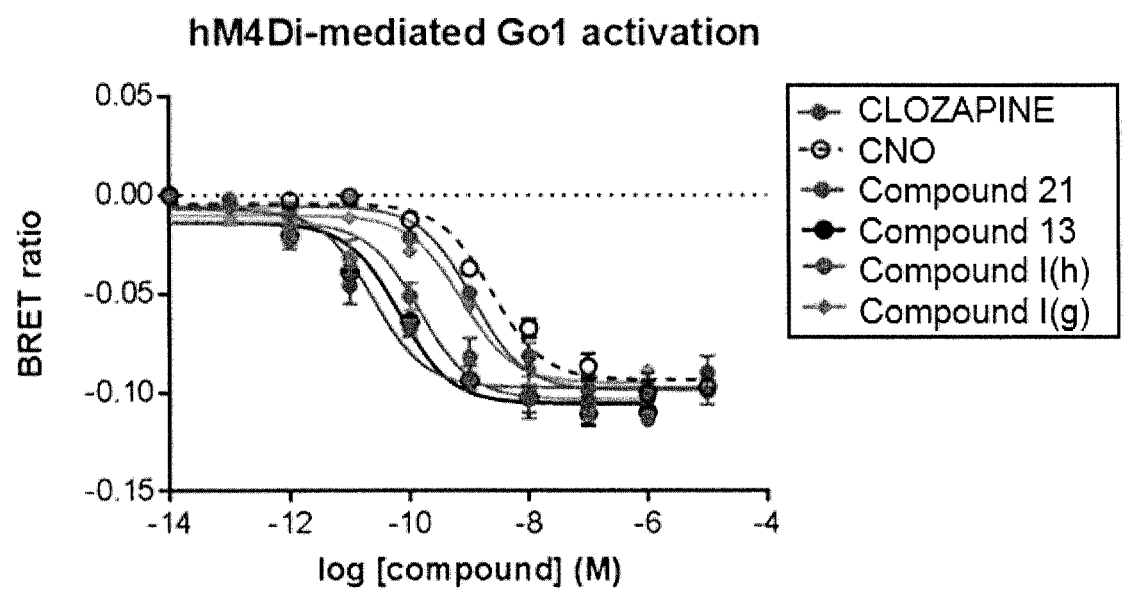
FIG. 8 is a graph showing the BRET of Go1 activation of clozapine, CNO, compound 13, compound 21, compound I(g), and compound I(h) on cells with hM4Di receptors.

FIG. 7 shows the BRET ratio of Go1 (another type of G protein) activation of clozapine, CNO, compound 13, compound 21, compound I(g), and compound I(h) on cells without DREADDs. FIG. 8 shows the BRET ratio of Go1 activation of clozapine, CNO, compound 13, compound 21, compound I(g), and compound I(h) on cells with hM4Di. Comparing FIG. 7 with FIG. 8 (and evaluating Table 3) reveals that compound I(g) and compound I(h) activate Go1.

TABLE 3

EC$_{50}$ value summary (in M) for hM4Di (Go1)

|  | mean | SEM |
|---|---|---|
| Clozapine | 5.60E−11 | 1.80E−11 |
| CNO | 3.10E−09 | 4.30E−10 |
| Compound 21 | 1.70E−09 | 6.00E−10 |
| Compound 13 | 6.30E−11 | 3.50E−12 |
| Compound I(g) [JHU37152] | 8.00E−10 | 1.20E−10 |
| Compound I(h) [JHU37160] | 1.40E−10 | 4.30E−11 |

Figure 9:
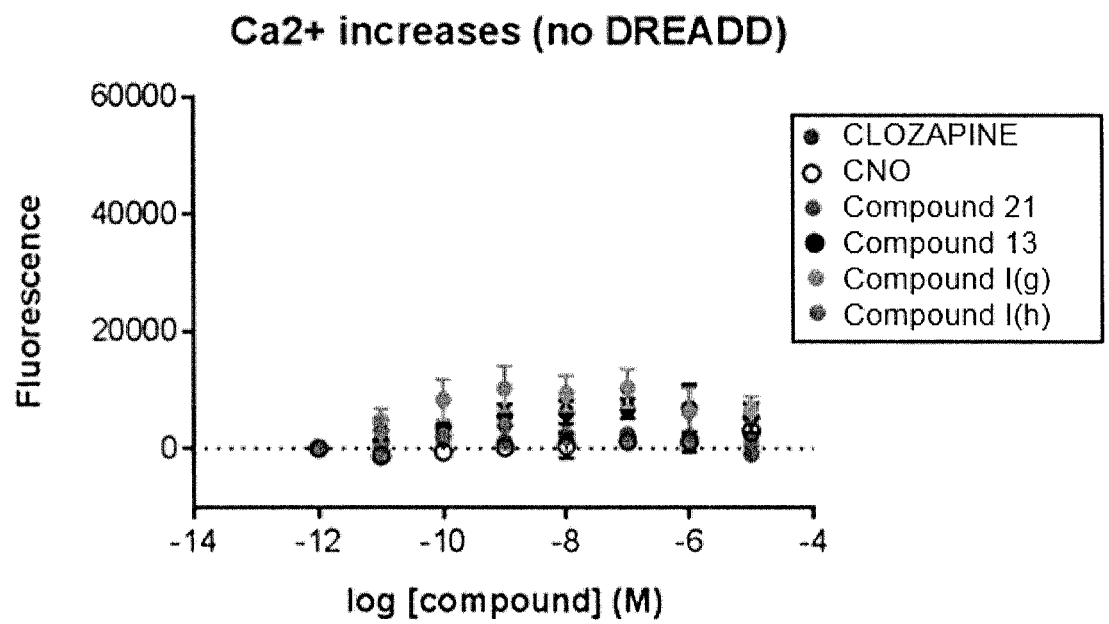
FIG. 9 is a graph showing the level of fluorescence in the calcium accumulation assay when clozapine, CNO, compound 13, compound 21, compound I(g), or compound I(h) is exposed to cells without DREADDs.
Figure 10:
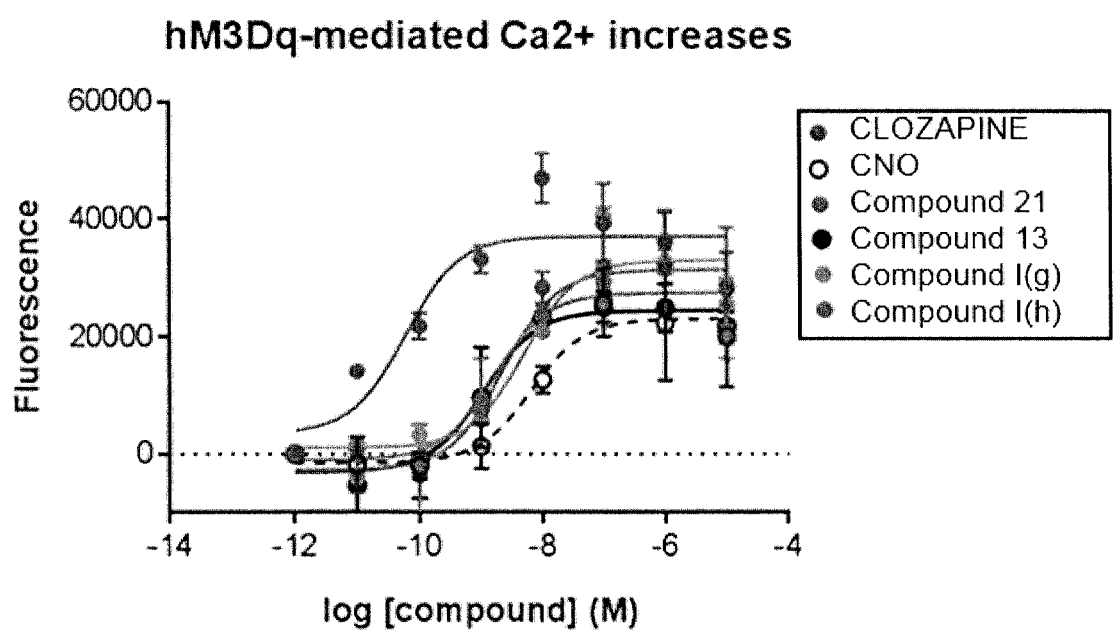
FIG. 10 is a graph showing the level of fluorescence in the calcium accumulation assay when clozapine, CNO, compound 13, compound 21, compound I(g), or compound I(h) is exposed to cells with hM3Dq.

FIG. 9 shows the level of fluorescence in the calcium accumulation assay when clozapine, CNO, compound 13, compound 21, compound I(g), or compound I(h) is exposed to cells without DREADDs. FIG. 10 shows the level of fluorescence in the calcium accumulation assay when clozapine, CNO, compound 13, compound 21, compound I(g), or compound I(h) is exposed to cells with hM3Dq. Comparing FIG. 9 with FIG. 10 (and evaluating Table 4) reveals that compound I(g) and compound I(h) are effective at activating hM3Dq.

TABLE 4

EC$_{50}$ value summary (in M) for hM3Dq

|  | mean | SEM |
|---|---|---|
| Clozapine | 3.77E−11 | 2.48E−11 |
| CNO | 1.13E−08 | 4.25E−09 |
| Compound 21 | 1.66E−09 | 1.75E−10 |
| Compound 13 | 1.43E−09 | 1.05E−09 |
| Compound I(g) [JHU37152] | 5.15E−09 | 1.13E−09 |
| Compound I(h) [JHU37160] | 2.64E−09 | 1.39E−09 |

Example 5

This example describes a locomotor activity assay (open-field test) which demonstrates that compound I(g) induces locomotor depression in mice with DREADDs.

Transgenic male and female mice (25-30 g, offspring of D1-Cre (heterozygous)×R26-hM3Dq/mCitrine (heterozygous) crossing) either heterozygous for both loci (CRE+, het het) or wild type for D1-Cre (CRE−, wt het) were tested for locomotor activity. The mice were injected (intraperitoneal) with the indicated dose of clozapine, compound I(g), or vehicle (buffered saline). Ten minutes after injection, animals were placed in an open field arena and their locomotor activity was tracked during 60 min as infra-red beam crossings. The animals were tested on consecutive sessions (after an initial habituation session with no drug treatment) and in a counterbalanced design.

Figure 11:
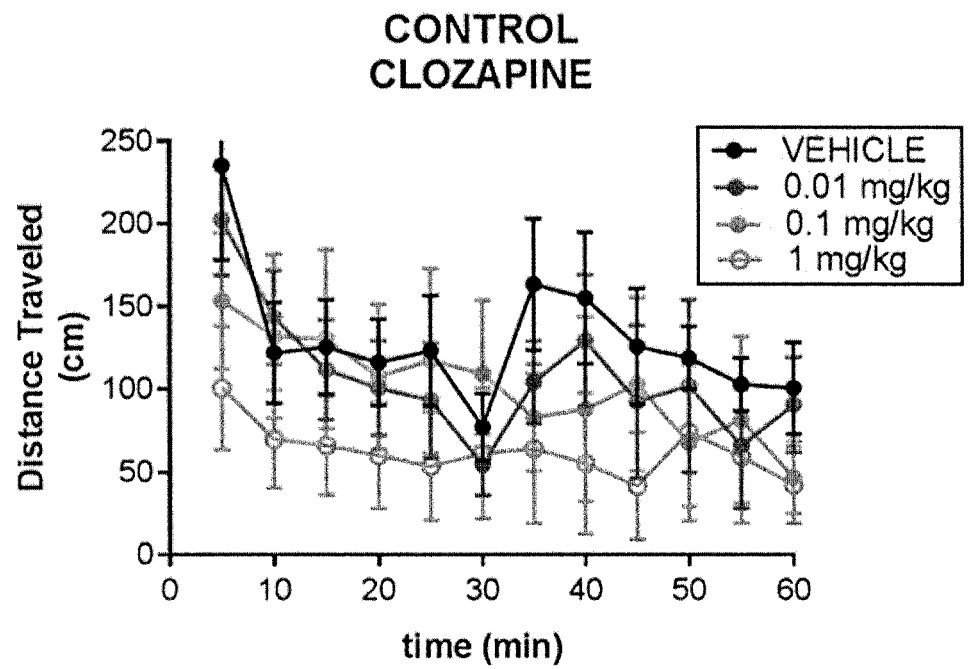
FIG. 11 is a graph showing the distance traveled in control mice (without hM3Dq receptors) that were injected with clozapine. The distance traveled in centimeters is on the y-axis, and the time in minutes is on the x-axis. The three amounts of clozapine (0.01, 0.1, and 1 mg/kg) administered and phosphate-buffered saline (PBS) (labeled "vehicle" in the legend) are plotted in the graph.
Figure 12:
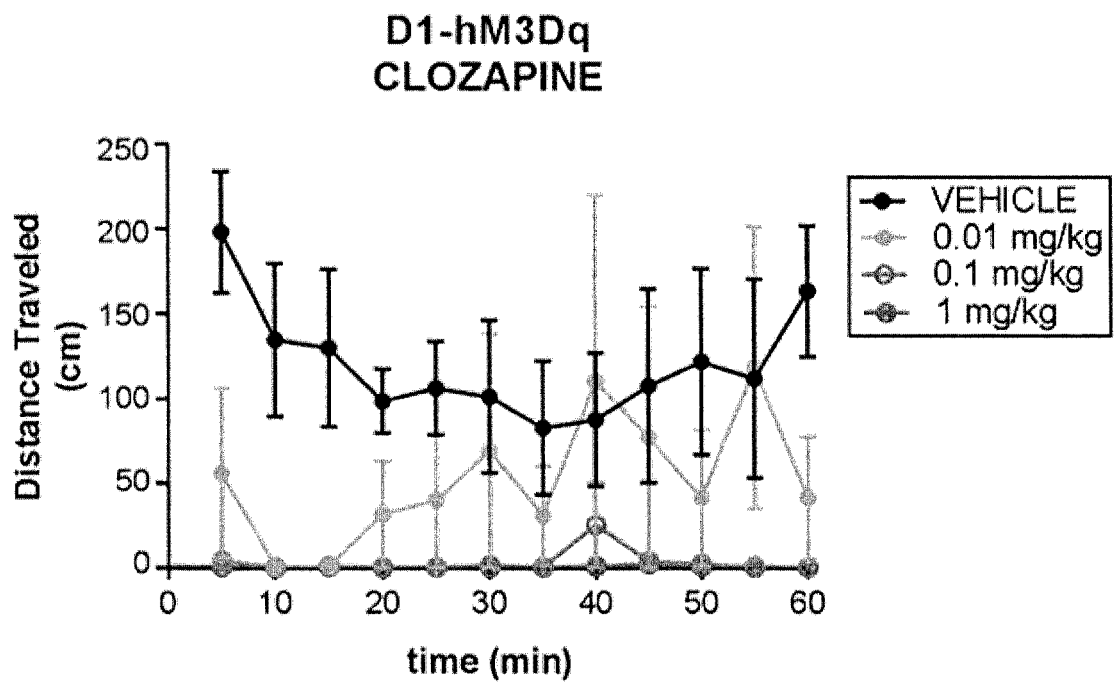
FIG. 12 is a graph showing the distance traveled of mice with hM3Dq receptors expressed in dopamine D1 receptor-expressing cells ("D1-hM3Dq") that were injected with clozapine. The distance traveled in centimeters is on the y-axis, and the time in minutes is on the x-axis. The three amounts of clozapine (0.01, 0.1, and 1 mg/kg) administered and PBS (labeled "vehicle" in the legend) are plotted in the graph.

FIG. 11 shows the distance traveled in control mice that were injected with clozapine. FIG. 12 shows the distance traveled in mice with D1-hM3Dq receptors that were injected with clozapine.

Figure 14:
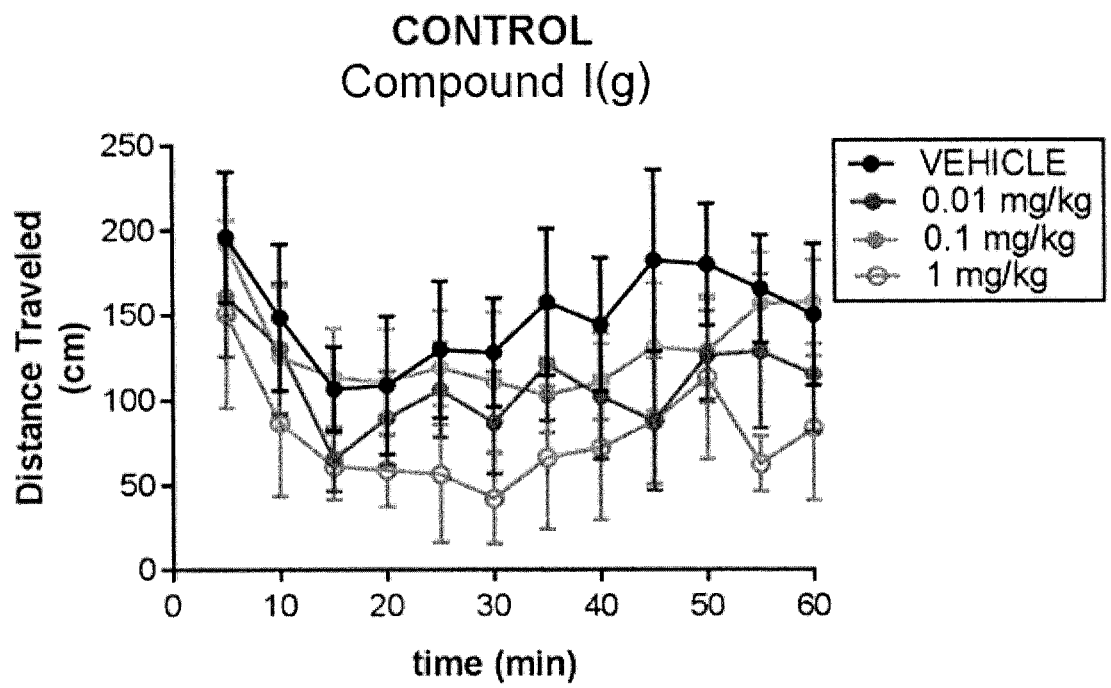
FIG. 14 is a graph showing the distance traveled in control mice (without hM3Dq receptors) that were injected with compound I(g). The distance traveled in centimeters is on the y-axis, and the time in minutes is on the x-axis. The three amounts of compound I(g) (0.01, 0.1, and 1 mg/kg) administered and PBS (labeled "vehicle" in the legend) are plotted in the graph.
Figure 15:
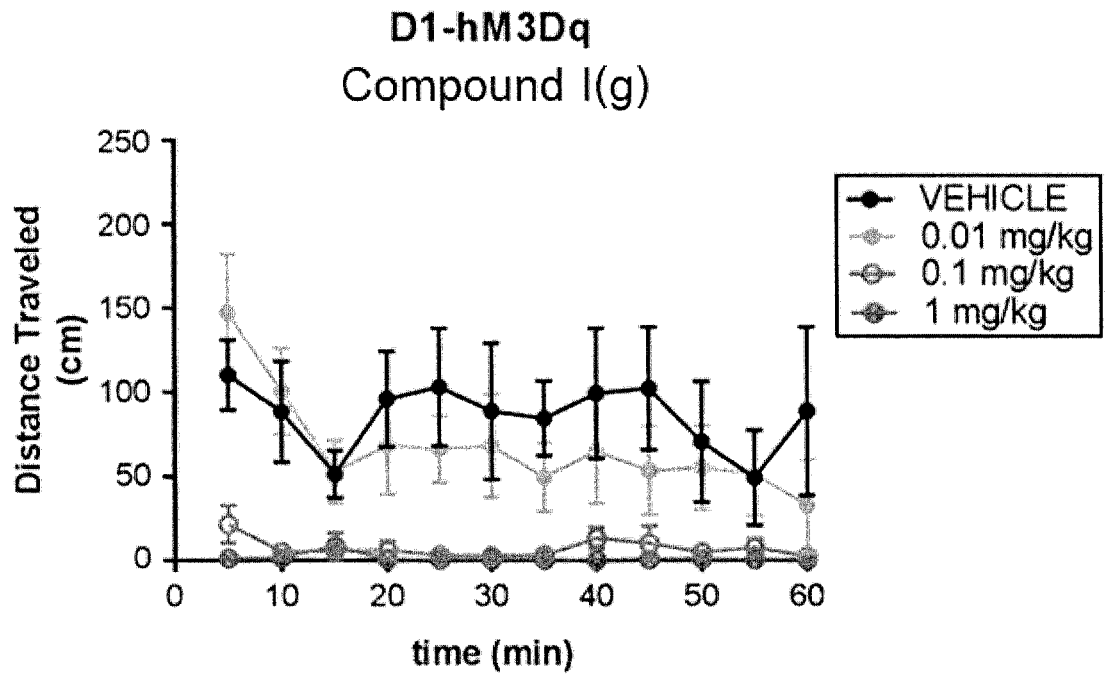
FIG. 15 is a graph showing the distance traveled in mice with D1-hM3Dq receptors that were injected with compound I(g). The distance traveled in centimeters is on the y-axis, and the time in minutes is on the x-axis. The three amounts of compound I(g) (0.01, 0.1, and 1 mg/kg) administered and PBS (labeled "vehicle" in the legend) are plotted in the graph.

FIG. 14 shows the distance traveled in control mice that were injected with compound I(g). FIG. 15 shows the distance traveled in mice with D1-hM3Dq receptors that were injected with compound I(g).

Figure 17:
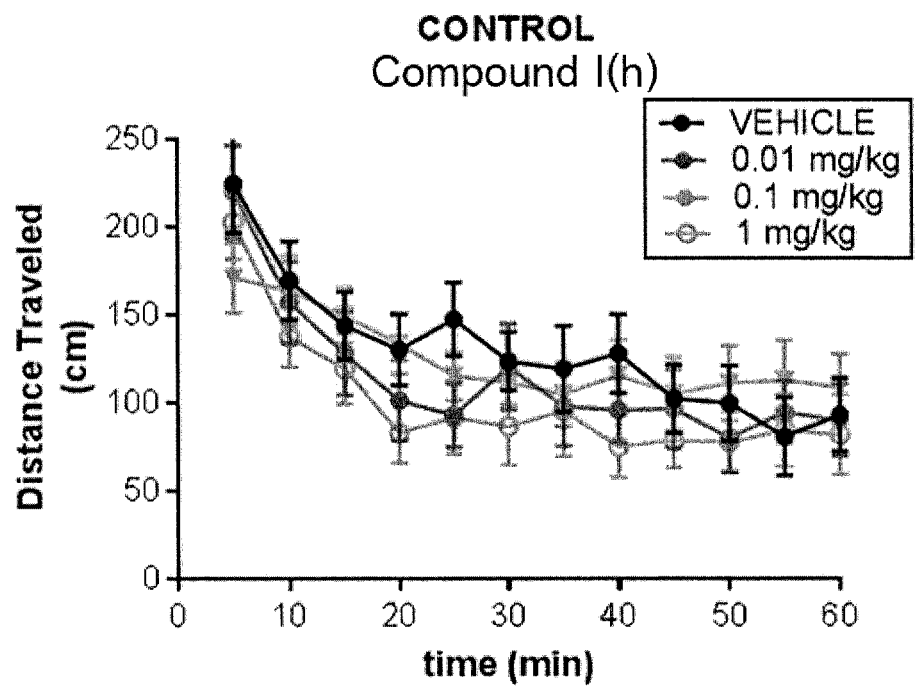
FIG. 17 is a graph showing the distance traveled in control mice (without hM3Dq receptors) that were injected with compound I(h). The distance traveled in centimeters is on the y-axis, and the time in minutes is on the x-axis. The three amounts of compound I(h) (0.01, 0.1, and 1 mg/kg) administered and PBS (labeled "vehicle" in the legend) are plotted in the graph.
Figure 18:
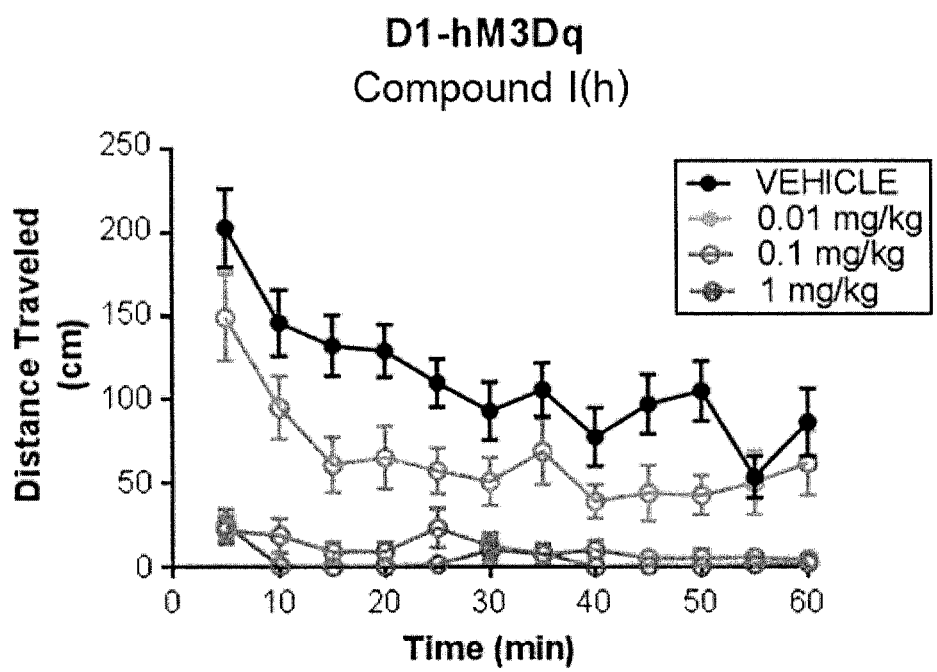
FIG. 18 is a graph showing the distance traveled in mice with D1-hM3Dq receptors that were injected with compound I(h). The distance traveled in centimeters is on the y-axis, and the time in minutes is on the x-axis. The three amounts of compound I(h) (0.01, 0.1, and 1 mg/kg) administered and PBS (labeled "vehicle" in the legend) are plotted in the graph.

FIG. 17 shows the distance traveled in control mice that were injected with compound I(h). FIG. 18 shows the distance traveled in mice with D1-hM3Dq receptors that were injected with compound I(h).

FIGS. 11-14 and 17-18 reveal that compound I(g) and compound I(h) are more effective than clozapine at reducing locomotor activity. These data suggest that compound I(g) and compound I(h) are effective at reducing anxiety in mice with hM3Dq receptors.

Figure 13:
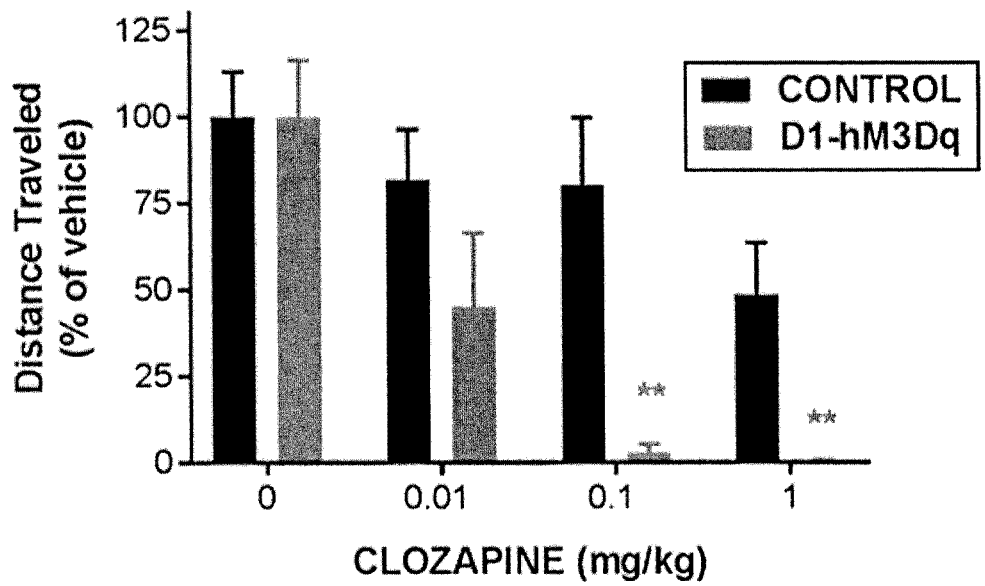
FIG. 13 is a graph showing the distance traveled (% of vehicle) when clozapine was administered. The amounts of clozapine administered (0, 0.01, 0.1, and 1 mg/kg) are listed on the x-axis, and the distance traveled, as a percentage of the vehicle (PBS), is on the y-axis. The control mice (without hM3Dq receptors) are represented by the grey bars, and the mice with hM3Dq receptors are represented by the black bars.
Figure 16:
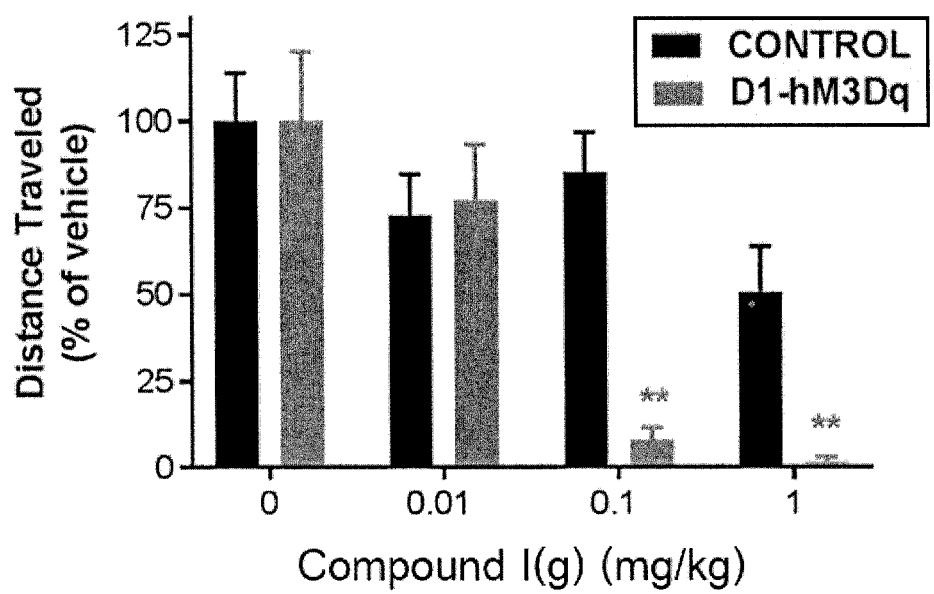
FIG. 16 is a graph showing the distance traveled (% of vehicle) when compound I(g) was administered. The amounts of compound I(g) administered (0, 0.01, 0.1, and 1 mg/kg) are listed on the x-axis, and the distance traveled, as a percentage of the vehicle (PBS), is on the y-axis. The control mice (without hM3Dq receptors) are represented by the grey bars, and the mice with hM3Dq receptors are represented by the black bars.
Figure 19:
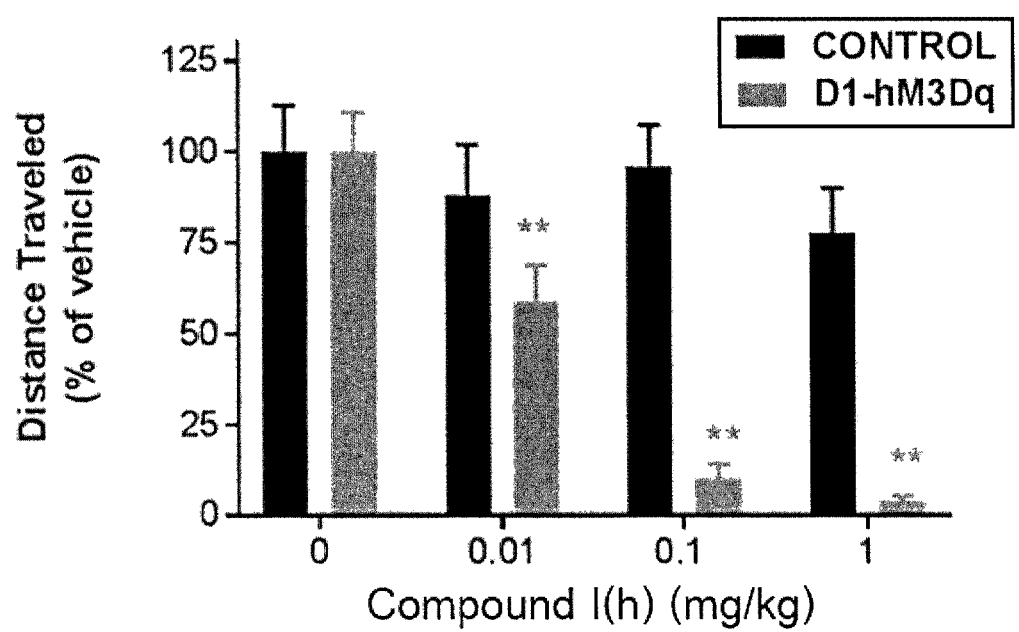
FIG. 19 is a graph showing the distance traveled (% of vehicle) when compound I(h) was administered. The amounts of compound I(h) administered (0, 0.01, 0.1, and 1 mg/kg) are listed on the x-axis, and the distance traveled, as a percentage of the vehicle (PBS), is on the y-axis. The control mice (without hM3Dq receptors) are represented by the grey bars, and the mice with hM3Dq receptors are represented by the black bars.

FIG. 13 shows the distance traveled (% of vehicle) when clozapine was administered. FIG. 16 shows distance traveled (% of vehicle) when compound I(g) was administered. FIG. 19 shows distance traveled (% of vehicle) when compound I(g) was administered. Comparing FIG. 13 with FIG. 16, and FIG. 13 with FIG. 19, reveals that compound I(g) and compound I(h) are more effective than clozapine at reducing locomotor activity. These data also suggest that compound I(g) and compound I(h) are effective at reducing anxiety in mice with hM3Dq receptors.

Example 6

This example demonstrates a suitable synthetic scheme for Compound [$^{18}$F]I(a).

Compound [$^{18}$F]I(a) was prepared via the no-carrier-added $^{18}$F-fluorination using an FDG Nuclear Interface module (Muenster, Germany). Briefly, 4 mg precursor (8-chloro-11-(4-ethylpiperazin-1-yl)-5H-dibenzo[b,e][1,4]diazepin-2-ol) and 8 mg tris(acetonitrile)cyclopentadienyl-ruthenium(II)hexafluorophosphate (STREM, Boston, Mass.) were dissolved in ethanol (0.3 mL), the solution was heated at 85 degrees C. for 25 min and evaporated to dryness under a stream of argon gas. The residue was dissolved in DMSO (0.5 mL) and acetonitrile (0.5 mL) and the solution was added to a dry complex of [$^{18}$F]fluoride and 9 mg 1,3-bis(2,6-di-i-propylphenyl)-2-chloroimidazolium chloride (STREM). The reaction mixture was heated at 130 degrees C. for 30 min, diluted with mixture of 0.5 mL acetonitrile, 0.5 mL water and 0.03 mL trifluoroacetic acid and injected onto a semi-preparative HPLC column (LUNA, Phenomenex, Inc., Torrance, Calif., C18, 10 micron, 10 mm×250 mm) and eluted with 23:77 (v:v) acetonitrile:water (0.1% trifluoroacetic acid) at a flow rate of 10 mL/min. The radioactive peak corresponding to Compound [$^{18}$F]I(a) (tR=9.9 min) was collected in a reservoir containing 50 mL of water and 3 mL aqueous 8.4% NaHCO$_3$ solution. The diluted product was loaded onto a solid phase extraction cartridge (OASIS HLB plus light, Waters Corp., Milford, Mass.) and rinsed with 10 mL sterile saline. The product was eluted with 1000 µL of ethanol through a sterile 0.2 µm filter into a sterile, pyrogen-free vial and 10 mL saline was added through the same filter. The final product, Compound [$^{18}$F]I(a), was then analyzed by analytical HPLC (LUNA, C18, 10 micron, 4.6 mm×250 mm; mobile phase 23:77 (v:v) acetonitrile:water (0.1% trifluoroacetic acid), flowrate of 3 mL/min; tR=6.4 min) using a UV detector at 254 nm to determine the radiochemical purity (>95%) and specific radioactivity (152-188 GBq/µmol (4,100-5,070 mCi/µmol)).

Example 7

This example demonstrates imaging of Compound [$^{18}$F]I(a) using positron emission tomography (PET).

Wild-type mice (C57BL/6J) were ordered from Jackson Laboratories and rats (Sprague-Dawley) were ordered from Charles River. Rodents were male and ordered at ~6-weeks of age. Transgenic mice were bred at NIDA breeding facility. Transgenic mice expressing the enzyme ere recombinase under the control of the dopamine D1 receptor promoter (D1-Cre, FK150 line, C57BL/6J congenic, Gensat, RRID: MMRRC_036916-UCD) were crossed with transgenic mice with cre recombinase-inducible expression of hM4Di DREADD (R26-hM4Di/mCitrine, Jackson Laboratory, stock no. 026219) or hM3Dq DREADD (R26-hM3Dq/mCitrine, Jackson Laboratory, stock no. 026220). Three male rhesus monkeys (Macaca mulatta) weighing 8-12 kg were used in this study.

Mice and rats were anesthetized with isoflurane and placed in a prone position on the scanner bed of an ARGUS small animal PET/CT (Sedecal, Spain) or a nanoScan PET/CT (Mediso Medical Imaging Systems, Budapest Hungary) and injected intravenously (100-200 L) with Compound [$^{18}$F]I(a) (~350 μCi) and dynamic scanning commenced. When indicated, animals were pretreated with vehicle or the indicated drug 10 min before the injection of the PET radiotracer. Total acquisition time was 60 min.

All macaque studies were acquired dynamically on the FOCUS 220 PET scanner (Siemens Medical Solutions, Knoxville, Tenn.). The Focus 220 is a dedicated pre-clinical scanner with a transaxial FOV of 19 cm and an axial FOV of 7.5 cm. Image resolution is <2 mm within the central 5 cm FOV.

After initial evaluation the monkey was sedated with ketamine (10 mg/kg) followed by ketoprofen (as an analgesic) and glycopyrrolate (for saliva reduction), all weight dependent IM injections. The monkey would then be placed in the supine position, intubated with a tracheal tube. Anesthesia was maintained by 1-3.5% isoflurane and oxygen, the monkey's head was positioned and immobilized for optimal positioning of the brain and moved into the scanner. A 10-minute transmission scan using a Co-57-point source for attenuation correction was performed. An intravenous catheter was inserted, if possible, in the right arm and another one in the right leg for injection of the tracer and blocking agent. The monkey was always monitored while anesthetized. Heart rate, blood pressure, $O_2$ saturation, respiration rate, 3 lead ECG, and rectal temperature were documented every 15 minutes. Arterial blood sampling was acquired throughout the study using an indwelling femoral port. The first two minutes samples were collected every 15 seconds then at 3, 5 10, 30, 60, 90, and 120 minutes post tracer injection. All scans were acquired for 120 minutes using list mode acquisition.

Scan data were histogrammed into 33 frames (6×30 seconds, 3×1 minute, 2×2 minutes and 22×5 minutes). Reconstruction was performed by Filtered Back Projection with scatter correction. After completion of the last study of the day, isoflurane was cut off. The monkey was gradually awakened, moved to the housing facility and fully recovered.

In all cases, the PET data were reconstructed and corrected for dead-time and radioactive decay. All qualitative and quantitative assessments of PET images were performed using the PMOD software environment (PMOD Technologies, Zurich Switzerland). Binding potential BPND (a relative measure of specific binding) was calculated using a reference tissue model using the cerebellum as a reference tissue in rodents. In macaques, the kinetic data were fitted to a two-tissue compartment model and the concentration of parent in plasma was used as an input function, then the volume of distribution ratios compared to cerebellum were calculated to establish BPND. In all cases, the dynamic PET images were coregistered to MRI templates and time-activity curves were generated using predefined volumes of interest (macaques) or manually drawn in rodents and the described analyses were performed. Receptor occupancy was calculated using the formula: Occupancy=(BPND0−BPNDDrug)/BPND0×100, where BPND0 is the binding potential of the baseline condition and BPNDDrug the binding potential when the animals were pretreated with the drug. In an independent manner, BPND parametric maps were generated by pixel-based kinetic modeling using a multilinear reference tissue model 18 using the cerebellum as a reference region and the start time (t*) was set to 16 min.

The arterial input function for the radiotracers injected in rhesus monkeys was determined using the general methods as previously described. The radioligand concentrations in the arterial plasma were corrected by the unchanged parent fraction.

Heparinized blood samples (0.5 mL each) were drawn at 15-s intervals until 2 minutes, and at 3, 5, 10, and 30 min followed by 3-mL samples at 60, 90, 120, 150, and 180 min. Blood samples were immediately sampled for gamma counting, and plasma harvested by centrifugation for gamma counting and radio-HPLC analysis. The unchanged plasma parent fractions were determined by radio-HPLC on an X-TERRA C18 column (10 μm, 7.8 mm×300 mm, Waters Corp.), and eluted with MeOH:H2O:Et3N (80:20:0.1; by volume) at an isocratic flow rate of 4.0 mL/min. Eluates were monitored with an in-line flow-through NaI(Tl) scintillation detector (Bioscan, Santa Barbara, Calif.). Data were stored and analyzed on a PC using the software Bio-ChromeLite (Bioscan). The collection of data for each radiochromatogram was decay corrected according to its respective HPLC injection time.

Monkey blood and CSF samples were collected from totally implanted subcutaneous access ports (Access Technologies, Richmond, Va.), connected to catheters indwelling in the femoral artery or intrathecal space of the spinal column, respectively. Rodent blood samples and brains were collected immediately following sacrifice at the indicated time points after intraperitoneal injection (10 ml/kg) in buffered saline. CSF was immediately frozen on dry ice and stored at −80 degrees C. Blood samples were allowed to coagulate for 15 minutes and then centrifuged at 4° C. for 15 minutes. Serum was collected from the supernatant and stored at a minimum of −30° C. until extraction. To 25 μl of serum, 5 μl of internal standard and 110 μl of methanol were added. Samples were centrifuged for 10 minutes at 16,200×g at 4 degrees C. and the supernatant was transferred to the autosampler vial for analysis. Brains were cut in half and weighed prior to sample preparation. Half brains were homogenized in 490 μl of 85% ethanol: 15% water containing 0.1% formic acid and 5 μl of internal standard using a polytron homogenizer and centrifuged for 10 minutes at 16,200×g at 4 degrees C. Three hundred μl of supernatant was dried under a stream of nitrogen and resuspended in 150 μl methanol. The resuspended solution was then centrifuged and 100 μl of supernatant was transferred to the autosampler vial for analysis.

Data was acquired using a NEXERA XR HPLC (Shimadzu Corporation, Kyoto, Japan) coupled with a QTRAP 6500 LC-MS/MS System (SCIEX, Framingham, Mass.) and was analyzed with Analyst 1.6 (SCIEX). The positive ion mode data was obtained using multiple reaction monitoring (MRM). The instrumental source setting for curtain gas, ion spray voltage, temperature, ion source gas 1, ion source gas 2 were 30 psi, 5500 V, 500 C, 650 psi, and 5560 psi, respectively. The collision activated dissociation was set to medium and the entrance potential was 10 V. Compound 21 was monitored using the MRM ion transition (278.80→166.10) with declustering potentials (DP)=90V, collision cell exit potentials (CXP)=10V and collision energies (CE)=50V. Compound I(g) and Compound I(h) were monitored using the MRM ion transitions (359.10→288.10) with DP=70V, CXP=8V and CE=28V. Clozapine was monitored using the MRM ion transitions (327.30→270.10) with DP=100V; 80V, CXP=11V and CE=40 V.

Separation of Compound 21, Compound I(g), Compound I(h), and clozapine was accomplished using a C18 Security guard cartridge (4.6×4 mm) and an ECLIPSE XDB-C18 column (4.6×250 mm, 5 µm, Agilent, Santa Clara, Calif.) at 35 degrees C. Mobile phase A consisted of water containing 0.1% formic acid and mobile phase B was methanol containing 0.1% formic acid. The following linear gradient was run for 21.0 min at a flow rate of 0.4 ml/min: 0-2.00 min 20% B, 7.0 min 80% B, 12 min 90% B, 18.0 min 90% B, 18.1 min 20% B. Twelve-point calibration curves were prepared in standard solution by a 0.5 serial dilution of standards from 0.92 µg/ml for Compound 21; 1 µg/ml for Compound I(h); 0.2 µg/ml for Compound I(g); and 0.4 µg/ml for clozapine. The injection volume per sample was 10 µl. Samples were kept at 4° C. in the autosampler tray prior to injection.

The data was measured using standard curves and quality controls, but it was not validated to ICH guidelines. The concentrations of Compound 21, Compound I(g), and Compound I(h) were measured using area ratios calculated with the internal standard clozapine (5 µl of 100 g/ml) and the concentrations of clozapine were measured using area ratios calculated with Compound I(h) as the internal standard (5 µl of 50 µg/ml). Quality control standards (low, middle and high) were prepared by adding the spiking standard to solution to 25 µl of serum and/or a half-brain and relative values are reported.

By utilizing PET with [$^{18}$F]fluorodeoxyglucose (FDG) to measure changes in regional metabolic activity, it was found that Compound 21 at an injected dose of 1 mg/kg resulted in significant changes in brain metabolic activity in WT mice. In contrast, utilizing PET with [$^{18}$F]fluorodeoxyglucose (FDG) revealed that Compound I(a) (0.1 mg/kg) produced opposing and differential recruitment of whole-brain functional networks in D1-hM3Dq and D1-hM4Di mice (n=4 mice per condition).

Further, Compound I(h) J60 (0.1 mg/kg) was found to produce rapid and potent hM4Di-driven inhibition of light-evoked neuronal activation.

Figure 23:
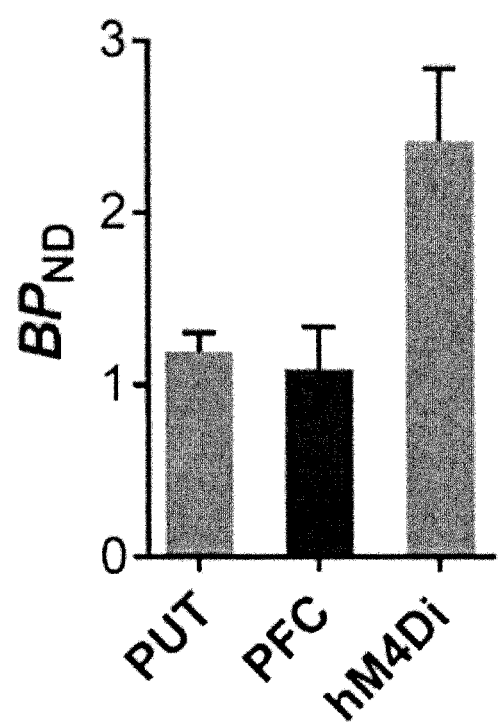
FIG. 23 is a graph showing that Compound [$^{18}$F]I(a) binds to hM4Di expressed in the macaque amygdala and at putative projection sites.

In addition, Compound [$^{18}$F]I(a) exhibited favorable pharmacokinetic properties and metabolite profile in the macaque where it was able to directly label hM4Di expressed in the amygdala and at putative axonal projection sites (see FIG. 23).

Accordingly, Compound [$^{18}$F]I(a) was found to be a potent DREADD agonist and a selective, high-affinity DREADD PET radioligand which can be used to advance the translational potential of DREADD technology.

Example 8

This example demonstrates DREADD-assisted metabolic mapping (DREAMM) using compounds of the present invention.

The study was set up as follows. Mice (D1-hM3Dq, D1-hM4Di or WT littermates) were habituated to experimenter handling and fasted 16 hours before the experiment. On the day of the experiment, mice received an IP injection of vehicle (1 ml/kg) and were placed back into their home cages. Ten minutes later, mice were injected (IP) with 11 MBq of 2-deoxy-2-[$^{18}$F]fluoro-D-glucose (FDG, Cardinal Health, Westmont, Ill.) and placed back into their home cages. After 30 minutes, mice were anesthetized with 1.5% isoflurane, placed on a custom-made bed of a NANOSCAN small animal PET/CT scanner (Mediso Medical Imaging Systems) and scanned for 20 min on a static acquisition protocol, followed by a CT scan. One week later the animals were fasted overnight, the next day received an IP injection of Compound 21 (1 mg/kg), clozapine (0.1 mg/kg) or Compound I(h) (0.1 mg/kg) and the FDG-PET procedure was conducted as described above. In all cases, the PET data were reconstructed and co-registered to an MRI template as described above. Voxel-based repeated measures with Student's t-test comparing baseline to drug were performed, and the resulting parametric images were filtered for statistically significant (p<0.05) clusters larger than 100 contiguous voxels. All statistical parametric mapping analyses were performed using MATLAB R2016 (Mathworks, Chicago, Ill.) and SPM12 (University College London).

Using DREAMM to assess neuronal activity, it was found that 0.1 mg/kg (IP) Compound I(h) produced metabolic changes in distinct and largely non-overlapping brain networks in D1-hM3Dq and D1-hM4Di mice and caused no significant brain metabolic changes in WT mice. DREAMM revealed the recruitment of distinct, almost mutually exclusive networks, paralleled by metabolic changes with opposite directionality upon differential modulation of D1 neurons with hM3Dq and hM4Di: decreased metabolism in D1-hM3Dq and increased metabolism in D1-hM4Di mice, effects likely mediated via activation and inhibition of striatal GABAergic D1-expressing neurons respectively.

In contrast, whole brain $^{18}$F-FDG metabolic mapping in WT mice showed decreased metabolic activity of multiple networks after a systemic administration of Compound 21 at 1 mg/kg.

Accordingly it was found that DREAMM can be used to evaluate, longitudinal, noninvasive assessment of whole-brain, functional circuit activity using compounds of the present invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of reducing locomotor activity in a subject in need thereof comprising administering a compound of, or a pharmaceutically acceptable salt thereof, to the subject, wherein the compound is of formula (III)

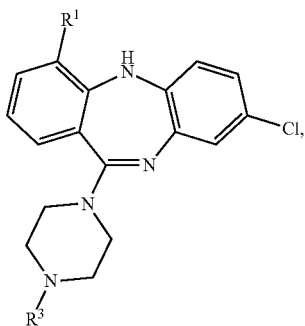

(III)

wherein $R^1$ is fluoro, bromo, or iodo, and $R^3$ is methyl or ethyl, or a pharmaceutically acceptable salt thereof.

2. The method of claim 1, wherein the subject expresses a DREADD-modified human muscarinic G-protein coupled receptor (GPCR), wherein the modified receptor is selected from the group consisting of hM3Dq and hM4Di.

3. A method for effectuating a G-protein coupled receptor (GPCR)-mediated response in a subject, the method comprising:
administering to the subject a vector encoding a DREADD-modified human muscarinic GPCR (hM-DREADD), wherein the modified receptor is selected from the group consisting of hM3Dq and hM4Di, to express the modified receptor, and
administering a compound, or a pharmaceutically acceptable salt thereof, to the subject, wherein the compound is of formula (III)

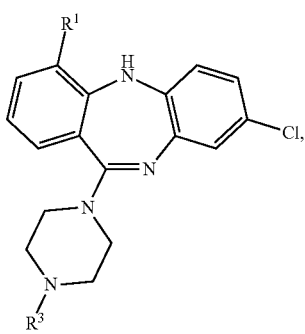

(III)

wherein $R^1$ is fluoro, bromo, or iodo, and $R^3$ is methyl or ethyl, or a pharmaceutically acceptable salt thereof.

4. The method of claim 3, further comprising:
imaging the subject by positron emission tomography.

5. The method of claim 4, further comprising:
comparing the level of expression of the modified receptor as determined by positron emission tomography to a control, and
adjusting the amount of the compound, or a pharmaceutically acceptable salt thereof, that is administered to the subject.

6. The method of claim 3, further comprising:
imaging the subject by magnetic resonance imaging (MRI), and optionally magnetic resonance spectroscopy.

7. The method of claim 6, further comprising:
comparing the level of expression of the modified receptor as determined by MRI to a control, and
adjusting the amount of the compound, or a pharmaceutically acceptable salt thereof, that is administered to the subject.

8. The method of claim 4, wherein $R^1$ is fluoro.

9. The method of claim 4, wherein the compound is

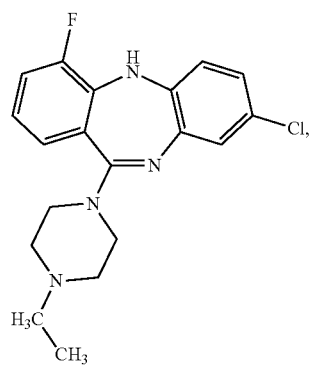

I(h)

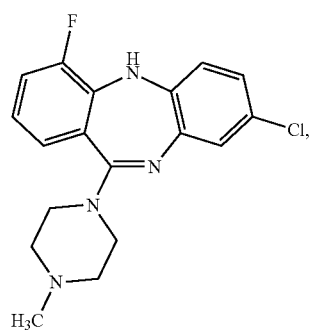

I(k)

or a pharmaceutically acceptable salt thereof.

10. The method of claim 4, wherein the compound is

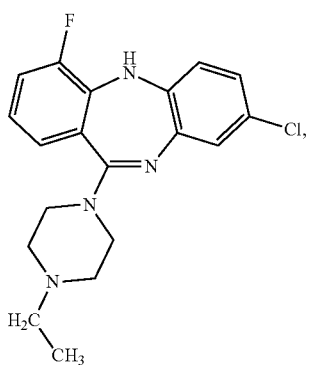

I(h)

or a pharmaceutically acceptable salt thereof.

11. The method of claim 4, wherein the compound is

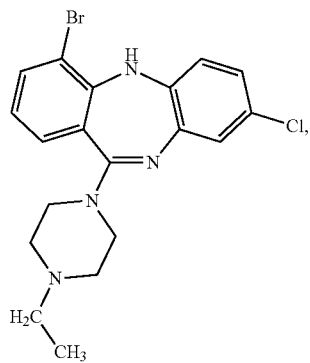

I(i)

or a pharmaceutically acceptable salt thereof.

12. The method of claim 11, wherein the bromo substituent is bromine-76 ($^{76}$B).

13. The method of claim 4, wherein the compound is

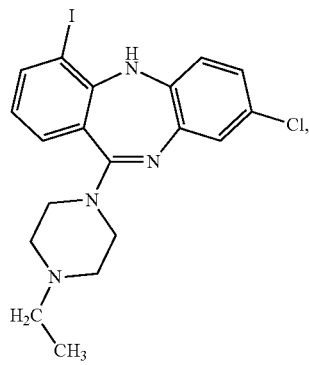

I(j)

or a pharmaceutically acceptable salt thereof.

14. The method of claim 13, wherein the iodo substituent is iodine-124 ($^{124}$I).

15. The method of claim 4, wherein the fluoro substituent is fluorine-18 ($^{18}$F).

16. The method of claim 4, wherein the method comprises administering a pharmaceutical composition comprising a pharmaceutically acceptable carrier and the compound, or a pharmaceutically acceptable salt of the compound, to the subject.

* * * * *